US008871802B2

(12) United States Patent
Jiang et al.

(10) Patent No.: US 8,871,802 B2
(45) Date of Patent: Oct. 28, 2014

(54) NAPHTHOQUINONES FOR DISEASE THERAPIES

(75) Inventors: Zhiwei Jiang, Stow, MA (US); Aijin Wang, West Roxbury, MA (US); Xian Li, Fengcheng (CN); Qingrong Li, FuYu Town (CN); Hongwei Hu, Suifenhe (CN); Jiali Xu, Tongcheng (CN); Yuesong Hu, Zhoushan (CN); Yan Ye, Zhoushan (CN)

(73) Assignee: Zhoushan HaiZhongZhou Xinsheng Pharmaceuticals Co., Ltd., Zhoushan (CN)

( * ) Notice: Subject to any disclaimer, the term of this patent is extended or adjusted under 35 U.S.C. 154(b) by 0 days.

(21) Appl. No.: 13/818,613

(22) PCT Filed: Aug. 24, 2010

(86) PCT No.: PCT/CN2010/001288
§ 371 (c)(1),
(2), (4) Date: Feb. 22, 2013

(87) PCT Pub. No.: WO2012/024818
PCT Pub. Date: Mar. 1, 2012

(65) Prior Publication Data
US 2013/0150437 A1  Jun. 13, 2013

(51) Int. Cl.
*A61K 31/343* (2006.01)
*C07D 307/92* (2006.01)
*A61K 45/06* (2006.01)

(52) U.S. Cl.
CPC ............ *A61K 31/343* (2013.01); *C07D 307/92* (2013.01); *A61K 45/06* (2013.01)
USPC ........... 514/468; 549/429; 549/456; 549/458; 514/449; 514/461

(58) Field of Classification Search
CPC ........................... C07D 307/92; A61K 31/343
USPC ........... 549/429, 456, 458; 514/449, 461, 468
See application file for complete search history.

(56) References Cited

U.S. PATENT DOCUMENTS

2006/0142271 A1  6/2006  Muller et al.
2013/0342176 A1  12/2013  Jiang et al.

FOREIGN PATENT DOCUMENTS

| CN | 1857251 A | 11/2006 |
| JP | 11-65141 A | 3/1999 |
| WO | WO-2006/088315 A1 | 8/2006 |
| WO | WO-2009036059 A2 | 3/2009 |

OTHER PUBLICATIONS

Zani et al (1998): STN International HCAPLUS database, (Columbus, Ohio), Accession No. 1998:34066.*
Koyanagi et al (1997): STN International HCAPLUS database, (Columbus, Ohio), Accession No. 1997: 706923.*
Berridge, M.V. and Tan, A.S., Characterization of the Cellular Reduction of 3-(4,5-dimethylthiazol-2-yl)-2,5-diphenyltetrazolium bromide (MTT): Subcellular Localization, Substrate Dependence, and Involvement of Mitochondrial Electron Transport in MTT Reduction, Archives of Biochemistry and Biophysics, 303(2): 474-482 (1993).
Desmond, J.C. et al., The synthetic furanonaphthoquinone induces growth arrest, apoptosis and differentiation in a variety of leukaemias and multiple myeloma cells. British Journal of Haematology, 131(4):520-9 (2005).
Ferreira, V.F. et al., NBS bromination reactions of dihydronaphthofuran quinones: a new fragmentation type reaction in the chemistry of quinones. Anais da Academia Brasileira Ciencias, 62(4):329-33 (1990).
Huot, R. and Brassard, P., Synthèse de méthyl-3 furoquinones, Canadian Journal of Chemistry, 52(1): 88-94 (1974).
International Search Report for PCT/CN2010/001288 mailed Jun. 2, 2011.
Kang, W-B et al., Regioselective Addition Reaction of Lithium Enolates to Thio-Substituted 1,4-Naphthoquinones. Convenient Synthesis of a Naphthofuran-4,9-dione Ring System, Chemistry Letters, 17(8): 1415-1418 (1988).
Koyanagi, J. et al., A short-step synthesis of naphtho[2,3-b]furan-4,9-dione, Journal of Heterocyclic Chemistry, 31(5): 1303-1304, (1994).
Kuo, H-S. et al., A Convenient Method for the Synthesis of Naphtho[2,3-b]furan-4,9-diones, Synthesis, 3: 188-9 (1979).
Mathieson, J. W. and Thomson, R. H., Naturally occurring quinones. Part XVIII. New spinochromes from Diadema antillarum, Spatangus purpureus, and Temnopleurus toreumaticus, Journal of the Chemical Society (C), 153-160 (1971).
Ogawa, M. et al., Cytotoxic activity toward KB cells of 2-substituted naphtho[2,3-b]furan-4,9-diones and their related compounds. Bioscience, Biotechnology, and Biochemistry, 70(4):1009-12 (2006).
Rao, M.M. and Kingston, D.G., Plant anticancer agents. XII. Isolation and structure elucidation of new cytotoxic quinones from *Tabebuia cassinoides*, Journal of Natural Products, 45(5):600-4 (1982).
Rivalle, C. et al., Furannes et pyrroles disubstitues en 2,3-XV : Synthese de benzo(f)furo(2,3-c)(10H)-oxepinones-4 et leur transformation en furonaphtoquinones, Tetrahedron, 30(17): 3193-3198 (1974).
Tisler, M. Heterocyclic Quinones in Advances in Heterocyclic Chemistry, ed. Katritzky, A.R., Academic Press, London, 45:56-63 (1989).
Tseng, C. et al., Furo[3',2':3,4]naphtho[1,2-d]imidazole derivatives as potential inhibitors of inflammatory factors in sepsis. Bioorganic and Medicinal Chemistry, 17:6773-6779 (2009).

* cited by examiner

*Primary Examiner* — Golam M M Shameem
(74) *Attorney, Agent, or Firm* — Choate, Hall & Stewart, LLP; Fangli Chen; John P. Rearick

(57) ABSTRACT

The present invention discloses novel naphtho[2,3-b]furan-4,9-diones and naphtho[2,3-b]thiophene-4,9-diones and methods of making and using the same. The present invention also discloses pharmaceutical compositions comprising novel naphtho[2,3-b]furan-4,9-dione or naphtho[2,3-b]thiophene-4,9-diones for the treatment of various indications including proliferative diseases.

25 Claims, No Drawings

NAPHTHOQUINONES FOR DISEASE THERAPIES

BACKGROUND OF THE INVENTION

Quinone-based compounds have a variety of biological activities. Some of them have been shown to have anti-cancer and other activities. For example, several natural occurring naphtho[2,3-b]furan-4,9-diones with interesting biological activities have been isolated from plants (Tisler, M. "Heterocyclic Quinones in Advances in Heterocyclic Chemistry" Vol. 45, ed. Katritzky, A. R., Academic Press, London, 1989, pp. 56-63), and 2-substituted naphtho[2,3-b]furan-4,9-diones have been found to have cytotoxic activity (Ogawa et al. Bioscience, Biotechnology, and Biochemistry, 2006, 70, 1009-1012).

As cancer is a leading cause of death worldwide, accounting for 13% of all deaths according to 2004 World Health Organization statistics, there remains a need for novel compounds useful for more effective treatment of cancer.

SUMMARY OF THE INVENTION

The present invention provides novel compounds that can be used for more effective treatment of cancer and other diseases, disorders and conditions.

Among other things, the present invention provides a compound of formula I:

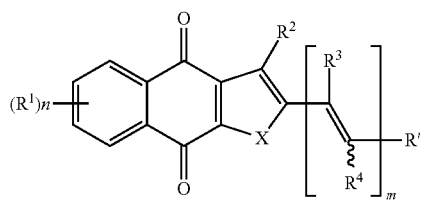

or a pharmaceutically acceptable salt thereof;
wherein each of $R^1$, $R^2$, $R^3$, $R^4$, X, R', n, and m is as defined herein.

The present invention also provides novel methods of synthesis of various compounds described herein. In addition, the present invention relates to pharmaceutical compositions comprising compounds described herein and the use of said compounds and compositions in the treatment of various diseases, disorders, and conditions.

DEFINITIONS

Certain compounds of the present disclosure, and definitions of specific functional groups are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

As used herein, the following definitions shall apply unless otherwise indicated.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. In certain embodiments, the term "3- to 14-membered carbocycle" and refers to a 3- to 8-membered saturated or partially unsaturated monocyclic carbocyclic ring, or a 7- to 14-membered saturated or partially unsaturated polycyclic carbocyclic ring.

The term "alkyl," as used herein, refers to saturated, straight- or branched-chain hydrocarbon derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms. In some embodiments, alkyl groups contain 1-4 carbon atoms. In certain embodiments, alkyl groups contain 1-3 carbon atoms. In some embodiments, alkyl groups contain 1-2 carbon atoms. Examples of alkyl group include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms. In some embodiments, alkenyl groups contain 2-4 carbon atoms. In some embodiments, alkenyl groups contain 2-3 carbon atoms. In some embodiments, alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

The term "acyl," used alone or a part of a larger moiety, refers to groups formed by removing a hydroxy group from a carboxylic acid.

The term "halogen" means F, Cl, Br, or I.

The term "aryl" used alone or as part of a larger moiety as in or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. In certain embodiments, the term "6- to 14-membered aryl" refers to a phenyl or an 8- to 14-membered polycyclic aryl ring.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or $14\pi$ is electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, fiiranyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The terms "heteroaralkyl" and "heteroarylalkyl" refer to an alkyl group substituted by a heteroaryl moiety, wherein the alkyl and heteroaryl portions independently are optionally substituted. In certain embodiments, the term "5- to 14-membered heteroaryl" refers to a 5- to 6-membered heteroaryl ring having 1 to 4 heteroatoms independently selected from nitrogen, oxygen, or sulfur, or an 8- to 14-membered polycyclic heteroaryl ring having 1 to 4 heteroatoms independently selected from nitrogen, oxygen, or sulfur.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl). In some embodiments, the term "3- to 14-membered heterocycle" refers to a 3- to 8-membered saturated or partially unsaturated monocyclic heterocyclic ring having 1 to 2 heteroatoms independently selected from nitrogen, oxygen, or sulfur, or a 7- to 14-membered saturated or partially unsaturated polycyclic heterocyclic ring having 1-3 heteroatoms independently selected from nitrogen, oxygen, or sulfur.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Unless otherwise stated, structures depicted herein are also meant to include all isomeric (e.g., enantiomeric, diastereomeric, and geometric (or conformational)) forms of the structure; for example, the R and S configurations for each stereocenter, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure.

If, for instance, a particular enantiomer of a compound of the present disclosure is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

When used as a chemical bond, "⌇" shall be understood to depict a single carbon-carbon bond with undefined stereochemistry at a carbon center. Thus, a substituent attached to a carbon atom with a "⌇" bond refers to embodiments where the substituent is coming out of the plane of the paper, embodiments where the substituent is going behind the plane of the paper, or combinations (i.e., stereochemical mixtures). In cases where a "⌇" bond is attached to a carbon-carbon double bond, it refers to either a Z or E double bond isomer or a mixture thereof.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this disclosure. Such compounds are useful, for example, as analytical tools, as probes in biological assays, or as therapeutic agents in accordance with the present disclosure.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NRO$_2$; —(CH$_2$)$_{0-4}$N(R°) C(O)OR°; —N(R°)N (R°)C(O)R°; —N(R°)N(R°)C(O)N R°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, —SC(S)SR°; —(CH$_2$)$_{0-4}$SC(O)R°; —(CH$_2$)$_{04}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)RO$_2$; —OP(O)R°$_2$; —OP(O)(OR°)$_2$; SiR°$_3$; —(C$_{1-4}$ straight or branched alkylene)O— N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6-membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(halon, R$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(halonR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6 membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(halonR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R' is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(halonR•), —OH, —OR•, —O(halonR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "amorphous" is used to describe the physical form of a solid in which there is no long-range order of the position of the atoms.

As used herein and in the claims, the singular forms "a", "an", and "the" include the plural reference unless the context clearly indicates otherwise. Thus, for example, a reference to "a compound" includes a plurality of such compounds.

The terms "administer," "administering," or "administration," as used herein, refer to either directly administering a compound or composition to a patient.

As used herein, the term "prodrug" means an agent that is converted into the parent drug in vivo. Prodrugs may be useful because, in some situations, they may be easier to administer than a parent drug. They may, for instance, have improved bioavailability by oral administration compared to the parent. Prodrugs may also have improved solubility in pharmaceutical compositions over the parent drug.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "palliative" refers to treatment that is focused on the relief of symptoms of a disease and/or side effects of a therapeutic regimen, but is not curative.

As used herein, the "blood-brain barrier" refers to the barrier between the peripheral circulation and the brain and spinal cord which is formed by tight junctions within the brain capillary endothelial plasma membranes, creates an extremely tight barrier that restricts the transport of molecules into the brain, even molecules as small as urea, molecular weight of 60 Da. The blood-brain barrier within the brain, the blood-spinal cord barrier within the spinal cord, and the blood-retinal barrier within the retina, are contiguous capillary barriers within the central nervous system (CNS), and are collectively referred to herein as the blood-brain barrier or BBB.

As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

The expression "unit dose" as used herein refers to a physically discrete unit of a formulation appropriate for a subject to be treated. It will be understood, however, that the total daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts. A particular unit dose may or may not contain a therapeutically effective amount of a therapeutic agent.

An individual who is "suffering from" a disease, disorder, and/or condition has been diagnosed with and/or displays one or more symptoms of the disease, disorder, and/or condition.

An individual who is "susceptible to" a disease, disorder, and/or condition has not been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition.

In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

DETAILED DESCRIPTION OF CERTAIN EMBODIMENTS

The present invention provides, among other thing, novel chemotherapeutics that are useful for the treatment of proliferative and other diseases, disorder, and conditions.

In certain embodiments, the present invention provides a compound of formula I:

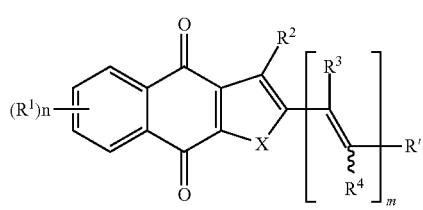

I or a pharmaceutically acceptable salt thereof;
wherein:
n is 0-4;
m is 0-2;
X is O or S;
each $R^1$ is independently halogen; $NO_2$; —CN; —OR; —SR; —N$^+$(R)$_3$; —N(R)$_2$; —C(O)R; —CO$_2$R; —C(O)C(O)R; —C(O)CH$_2$C(O)R; —S(O)R; —S(O)$_2$R; —C(O)N(R)$_2$; —SO$_2$N(R)$_2$; —OC(O)R; —N(R)C(O)R; —N(R)N(R)$_2$; —N(R)C(=NR)N(R)$_2$; —C(=NR)N(R)$_2$; C=NOR; —N(R)C(O)N(R)$_2$; —N(R)SO$_2$N(R)$_2$; —N(R)SO$_2$R; —OC(O)N(R)$_2$; or an optionally substituted group selected from $C_{1-12}$ aliphatic; a 3- to 14-membered carbocycle; a 3- to 14-membered heterocycle; a 6- to 14-membered aryl ring; or a 5- to 14-membered heteroaryl ring, or:
two $R^1$ groups on adjacent carbon atoms are taken together with their intervening atoms to form an optionally substituted ring selected from 3- to 14-membered carbocycle; 3- to 14-membered heterocycle; a 6- to 14-membered aryl ring; or a 5- to 14-membered heteroaryl ring;
each $R^2$, $R^3$, and $R^4$ is independently hydrogen; halogen; —NO$_2$; —CN; —OR; —SR; —N$^+$(R)$_3$; —N(R)$_2$; —C(O)R; —CO$_2$R; —C(O)C(O)R; —C(O)CH$_2$C(O)R; —S(O)R; —S(O)$_2$R; —C(O)N(R)$_2$; —SO$_2$N(R)$_2$; —OC(O)R; —N(R)C(O)R; —N(R)N(R)$_2$; —N(R)C(=NR)N(R)$_2$; —C(=NR)N(R)$_2$; —C NOR; —N(R)C(O)N(R)$_2$; —N(R)SO$_2$N(R)$_2$; —N(R)SO$_2$R; —OC(O)N(R)$_2$; or an optionally substituted group selected from $C_{1-12}$ aliphatic; a 3- to 14-membered carbocycle; a 3- to 14-membered heterocycle; a 6- to 14-membered aryl ring; or a 5- to 14-membered heteroaryl ring;
R' is —S(O)R$^5$; —S(O)$_2$R$^5$; or —NO$_2$, wherein when m is 0, R' is —S(O)R$^5$ or —S(O)$_2$R$^5$;
$R^5$ is —OR; —SR; —N(R)$_2$; or an optionally substituted group selected from $C_{1-12}$ aliphatic; a 3- to 14-membered carbocycle; a 3- to 14-membered heterocycle; a 6- to 14-membered aryl ring; or a 5- to 14-membered heteroaryl ring; and each R is independently hydrogen or an optionally substituted group selected from $C_{1-12}$ aliphatic; a 3- to 14-membered carbocycle; a 3- to 14-membered heterocycle; a 6- to 14-membered aryl ring; or a 5- to 14-membered heteroaryl ring.

In some embodiments, n is 0. In some embodiments, n is 1. In some embodiments, n is 2. In some embodiments, n is 3. In some embodiments, n is 4.

In certain embodiments, $R^1$ is halogen. In some embodiments, $R^1$ is —CN. In some embodiments, $R^1$ is —CF$_3$.

In some embodiments, $R^2$ is hydrogen. In some embodiments, $R^2$ is other than hydrogen. In some embodiments, $R^2$ is an optionally substituted 6- to 14-membered aryl ring. In some embodiments, $R^2$ is optionally substituted phenyl. In some embodiments, $R^2$ is optionally substituted amine.

In some embodiments, $R^3$ is hydrogen. In some embodiments, $R^3$ is other than hydrogen. In some embodiments, $R^3$ is hydroxyl. In some embodiments, $R^3$ is optionally substituted $C_{1-12}$ aliphatic. In some embodiments, $R^3$ is optionally substituted $C_{1-6}$ aliphatic. In some embodiments, $R^3$ is methyl.

In some embodiments, $R^4$ is hydrogen. In some embodiments, $R^4$ is other than hydrogen. In some embodiments, $R^4$ is optionally substituted $C_{1-12}$ aliphatic. In some embodiments, $R^4$ is optionally substituted $C_{1-6}$ aliphatic. In some embodiments, $R^4$ is methyl.

In certain embodiments, R' is —S(O)R$^5$. In some embodiments, R' is —S(O)$_2$R$^5$. In some embodiments, R' is —NO$_2$ when m is not 0.

In certain embodiments, $R^5$ is optionally substituted $C_{1-12}$ aliphatic. In some embodiments, $R^5$ is optionally substituted $C_{1-6}$ aliphatic. In some embodiments, $R^5$ is methyl. In certain embodiments, $R^5$ is —CF$_3$. In some embodiments, $R^5$ is an optionally substituted 6- to 14-membered aryl ring. In certain embodiments, $R^5$ is optionally substituted phenyl. In some embodiments, $R^5$ is phenyl substituted with halogen. In some embodiments, $R^5$ is phenyl substituted with fluoro. It will be appreciated that $R^5$, among other groups, may comprise a moiety that forms a salt with a suitable chemical partner. For example, in certain embodiments, $R^5$ comprises an amine group that forms a salt with a suitable conjugate acid.

In certain embodiments, m is 0. In some embodiments, m is 1. In other embodiments, m is 2.

In certain embodiments, X is O. In certain embodiments, X is S.

In some embodiments, R' is halogen, cyano, or CF$_3$, n is 0, 1, or 2, $R^2$ is hydrogen or —N(R)$_2$, $R^3$ is hydrogen or hydroxyl, $R^4$ is hydrogen or methyl, R' is —S(O)R$^5$ or —S(O)$_2$R$^5$, $R^5$ is methyl, tert-butyl, CF$_3$, or optionally substituted 6- to 14-membered aryl, X is oxygen, and m is 0 or 1. In some embodiments, R' is halogen or CF$_3$, n is 0, 1, or 2, $R^2$ is hydrogen, $R^3$ is hydrogen or hydroxyl, $R^4$ is hydrogen, R' is —S(O)R$^5$ or —S(O)$_2$R$^5$, $R^5$ is methyl or tert-butyl, X is oxygen, and m is 0 or 1. In some embodiments, $R^1$ is halogen or CF$_3$, n is 0 or 1, $R^2$ is hydrogen, $R^3$ is hydroxyl, $R^4$ is hydrogen, R' is —S(O)R$^5$ or —S(O)$_2$R$^5$, $R^5$ is methyl, X is oxygen, and m is 0 or 1. In some embodiments, R' is halogen or CF$_3$, n is 0 or 1, $R^2$ is hydrogen, $R^3$ is hydroxyl, $R^4$ is hydrogen, $R_1$ is —NO$_2$, X is oxygen, and m is 1.

It will be understood that for a compound of formula I when m is 1, a "〰" bond indicates that a double bond may be of Z stereochemistry or E stereochemistry. In certain embodiments, provided compounds are of formula I-a or I-b:

I-a

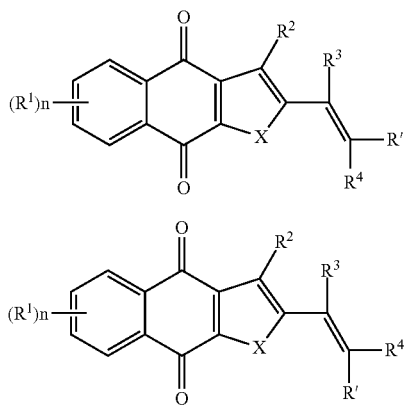

I-b

Similarly, for a compound of formula I when m is 2, a "⁓" bond indicates that each double bond may be independently of Z stereochemistry or E stereochemistry. In certain embodiments, provided compounds are of formula I-c, I-d, I-e, or I-f:

I-c

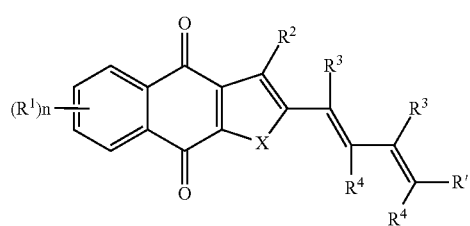

I-d

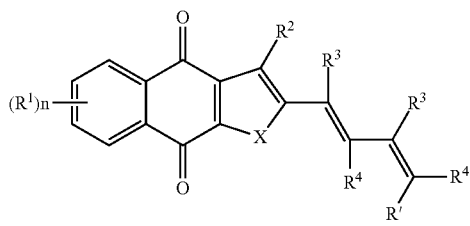

I-e

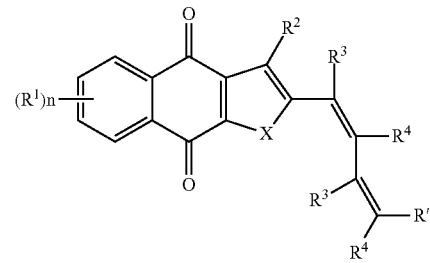

I-f

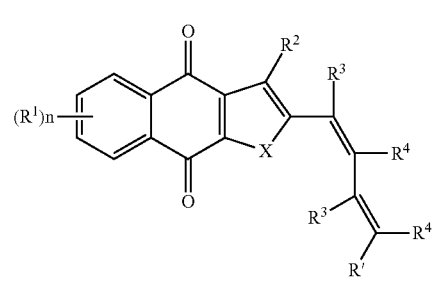

Exemplary compounds of formula I are set forth in Table 1 below.

TABLE 1 compound I

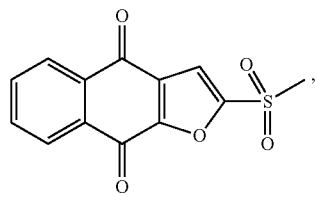 [SMILES: CS(=O)(=O)c1cc2c(o1)C(=O)c1ccccc1C2=O]

compound II

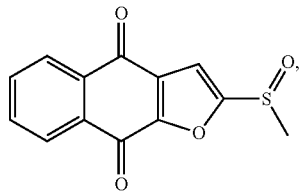 [SMILES: CS(=O)c1cc2c(o1)C(=O)c1ccccc1C2=O]

compound III

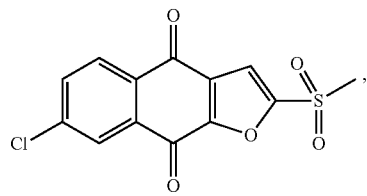 [SMILES: CS(=O)(=O)c1cc2c(o1)C(=O)c1cc(Cl)ccc1C2=O]

Compound IV

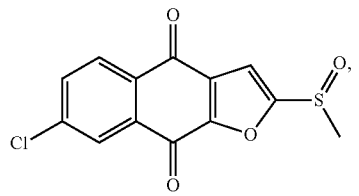 [SMILES: CS(=O)c1cc2c(o1)C(=O)c1cc(Cl)ccc1C2=O]

compound V

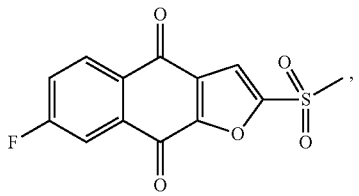 [SMILES: CS(=O)(=O)c1cc2c(o1)C(=O)c1cc(F)ccc1C2=O]

compound VI

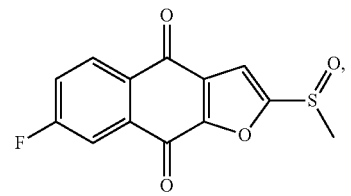 [SMILES: CS(=O)c1cc2c(o1)C(=O)c1cc(F)ccc1C2=O]

TABLE 1-continued
compound VII
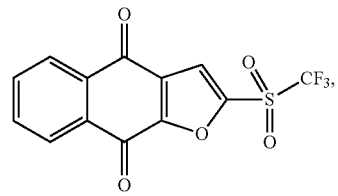 [SMILES: O=C1c2ccccc2C(=O)c2oc(S(=O)(=O)C(F)(F)F)cc21]
compound VIII
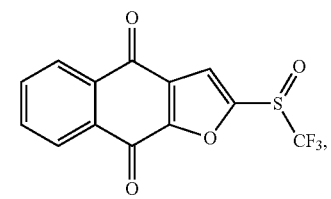 [SMILES: O=C1c2ccccc2C(=O)c2oc(S(=O)C(F)(F)F)cc21]
compound IX
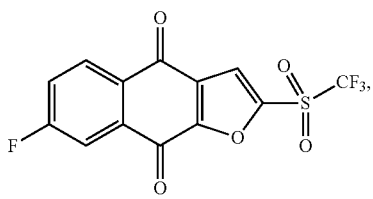 [SMILES: O=C1c2ccc(F)cc2C(=O)c2oc(S(=O)(=O)C(F)(F)F)cc21]
compound X
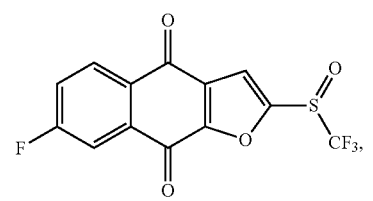 [SMILES: O=C1c2ccc(F)cc2C(=O)c2oc(S(=O)C(F)(F)F)cc21]
compound XI
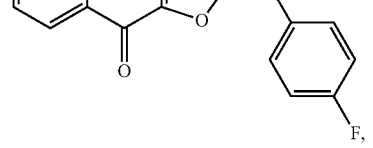
compound XII
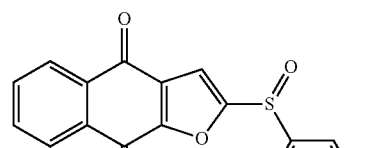
TABLE 1-continued
compound XIII
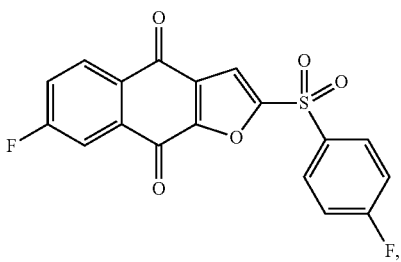 [SMILES: O=C1c2ccc(F)cc2C(=O)c2oc(S(=O)(=O)c3ccc(F)cc3)cc21]
compound XIV
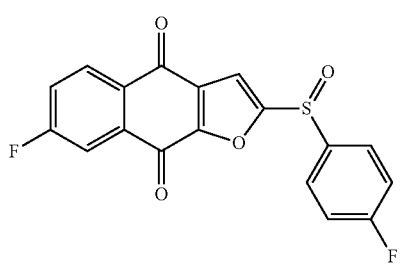 [SMILES: O=C1c2ccc(F)cc2C(=O)c2oc(S(=O)c3ccc(F)cc3)cc21]
compound XV
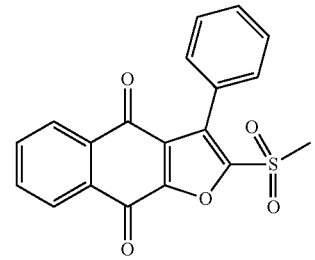 [SMILES: CS(=O)(=O)c1oc2c(c1-c1ccccc1)C(=O)c1ccccc1C2=O]
compound XVI
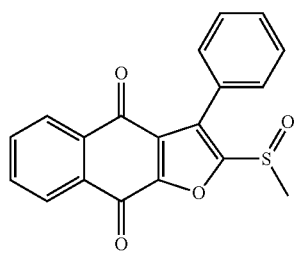 [SMILES: CS(=O)c1oc2c(c1-c1ccccc1)C(=O)c1ccccc1C2=O]
compound XVII
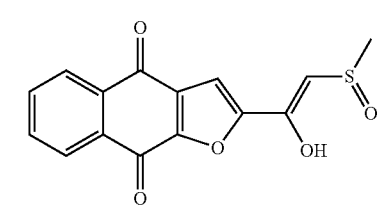

TABLE 1-continued

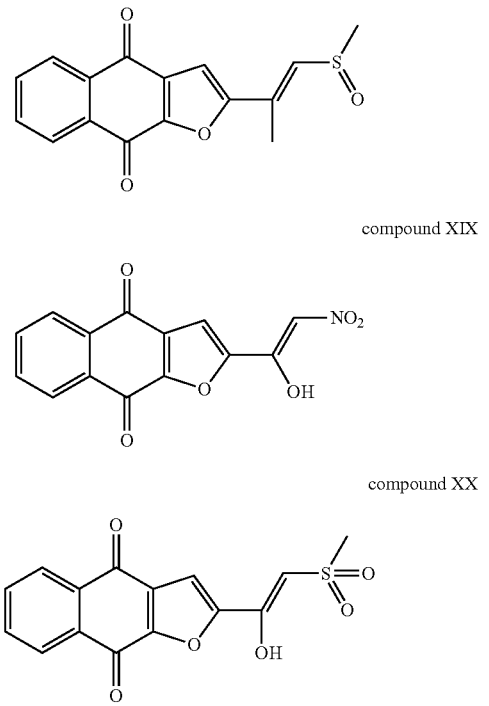

compound XVIII compound XIX compound XX

In some embodiments, provided compounds are 2-sulfonyl substituted naphtho[2,3-b]furan-4,9-diones. In some embodiments, provided compounds are 2-sulfinyl substituted naphtho[2,3-b]furan-4,9-diones. In some embodiments, provided compounds are 2-(1-hydroxy-2-nitroethenyl) substituted naphtho[2,3-b]furan-4,9-diones. In some embodiments, provided compounds are 2-(1-hydroxy-2-methylsulfinylethenyl) substituted naphtho[2,3-b]furan-4,9-diones. In some embodiments, provided compounds are 2-(1-hydroxy-2-methylsulfonylethenyl) substituted naphtho[2,3-b]furan-4,9-diones. In some embodiments, provided compounds are 2-(1-methyl-2-methylsulfinylethenyl) substituted naphtho[2,3-b]furan-4,9-diones. In some embodiments, provided compounds are 2-sulfonyl substituted naphtho[2,3-b]thiophene-4,9-diones. In some embodiments, provided compounds are 2-sulfinyl substituted naphtho[2,3-b]thiophene-4,9-diones.

Synthesis

The present invention also provide novel methods for synthesizing novel compounds described herein.

Prior to the present invention, there are numerous reports about synthesis of naphtho[2,3-b]furan-4,9-diones (Journal of Natural Products, 1982, 45, 600-4; US 2006/0142271; WO 2009036059; Bioscience, Biotechnology, and Biochemistry, 2006, 70, 1009-1012; J. Chem. Soc., 1971, C, 153; Tetrahedron, 1974, 30, 3193; An. Acad. Bras. Cienc., 1990, 62, 329; J. Hererocyclic Chem., 1994, 31, 1303-1304; Canadian Journal of Chemistry, 1974, 52, 88-94; Synthesis, 1979, 3, 188-9; Chemistry Letters, 1988, 8, 1415-18; British Journal of Haematology, 2005, 131, 520-529). However, most of the reported methods are useful only for fixed substituent groups at position 2 or for substituent groups with limited variations at position 2 (Journal of Natural Products, 1982, 45, 600-4; US 2006/0142271; WO 2009036059; Bioscience, Biotechnology, and Biochemistry, 2006, 70, 1009-1012; Canadian Journal of Chemistry, 1974, 52, 88-94; Synthesis, 1979, 3, 188-9; Chemistry Letters, 1988, 8, 1415-18; British Journal of Haematology, 2005, 131, 520-529). In order to obtain variety types of substituent groups at position 2, it is useful to synthesize position 2 unsubstituted naphtho[2,3-b]furan-4,9-dione. There are only a few reported methods for synthesis of such naphtho[2,3-b]furan-4,9-dione (J. Chem. Soc., 1971, C, 153; Tetrahedron, 1974, 30, 3193; An. Acad. Bras. Cienc., 1990, 62, 329; J. Herterocyclic Chem., 1994, 31, 1303-1304), and these methods require multiple reaction steps and low overall yield.

The present invention provides, among other things, novel and/or improved methods of preparing position 2 unsubstituted naphtho[2,3-b]furan-4,9-diones. In some embodiments, sulfonyl ethylene, nitro ethylene, or sulfinyl ethylene or their derivatives as the starting material to which bromine, base, 2-hydroxy-1,4-naphthoquinone and base are added successively in one pot synthesis to yield position 2 unsubstituted naphtho[2,3-b]furan-4,9-dione.

In certain embodiments, the present invention provides methods of synthesizing position 2-unsubstituted naphtho[2,3-b]furan-4,9-diones (compound of formula D) by using compound of formula A (sulfonyl ethylene or nitro ethylene or sulfinyl ethylene or their derivatives) as one of starting materials as shown in the Scheme I.

Scheme I:

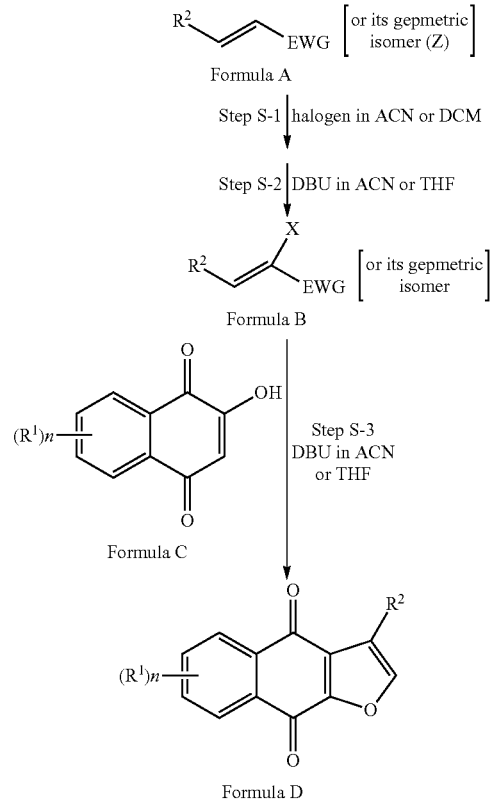

wherein:
n is 0-4;
each $R^1$ is independently halogen; —$NO_2$; —CN; —OR; —SR; —$N^+(R)_3$; —$N(R)_2$; —C(O)R; —$CO_2R$; —C(O)C(O)R; —C(O)$CH_2$C(O)R; —S(O)

R; —S(O)₂R; —C(O)N(R)₂; —SO₂N(R)₂; —OC(O)R; —N(R)C(O)R; —N(R)N(R)₂; —N(R)C(=NR)N(R)₂; —C(=NR)N(R)₂; —C=NOR; —N(R)C(O)N(R)₂; —N(R)SO₂N(R)₂; —N(R)SO₂R; —OC(O)N(R)₂; or an optionally substituted group selected from C₁₋₁₂ aliphatic; a 3- to 14-membered carbocycle; a 3- to 14-membered heterocycle; a 6- to 14-membered aryl ring; or a 5- to 14-membered heteroaryl ring, or: two R¹ groups on adjacent carbon atoms are taken together with their intervening atoms to form an optionally substituted ring selected from 3- to 14-membered carbocycle; 3- to 14-membered heterocycle; a 6- to 14-membered aryl ring; or a 5- to 14-membered heteroaryl ring;

R² is hydrogen; halogen; —NO₂; —CN; —OR; —SR; —N⁺(R)₃; —N(R)₂; —C(O)R; —CO₂R; —C(O)C(O)R; —C(O)CH₂C(O)R; —S(O)R; —S(O)₂R; —C(O)N(R)₂; —SO₂N(R)₂; —OC(O)R; —N(R)C(O)R; —N(R)N(R)₂; —N(R)C(=NR)N(R)₂; —C(=NR)N(R)₂; —C=NOR; —N(R)C(O)N(R)₂; —N(R)SO₂N(R)₂; —N(R)SO₂R; —OC(O)N(R)₂; or an optionally substituted group selected from C₁₋₁₂ aliphatic; a 3- to 14-membered carbocycle; a 3- to 14-membered heterocycle; a 6- to 14-membered aryl ring; or a 5- to 14-membered heteroaryl ring;

EWG is —S(O)₂R⁵; NO₂; —S(O)R⁵;

X is —Br or —I;

R⁵ is an optionally substituted group selected from C₁₋₁₂ aliphatic; a 3- to 14-membered carbocycle; a 3- to 14-membered heterocycle; a 6- to 14-membered aryl ring; or a 5- to 14-membered heteroaryl ring.

In Scheme I, a compound of formula A (sulfonyl ethylene or nitro ethylene or sulfinyl ethylene or their derivatives) or a compound of formula A precursor is used as starting material to which halogen, base, 2-hydroxy-1,4-naphthoquinone (i.e., a compound of formula C) and base are added successively in one pot synthesis to yield a compound of formula D, position 2 unsubstituted naphtho[2,3-b]furan-4,9-dione. In some embodiments, a compound of formula B is formed in situ and not isolated. In some embodiments, a compound of formula B is isolated. In some embodiments, the synthesis of compound of formula D begins with compound of formula B without use of a compound of formula A.

In some embodiments, a compound of formula A is a compound of formula VI-a:

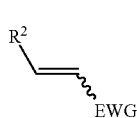

VI-a wherein each of EWG, R², and R⁵ is as described above for Scheme I.

In some embodiments, a compound of formula B is a compound of formula VII-a:

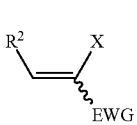

VII-a wherein each of X, R² and EWG is as described above for Scheme I.

In certain embodiments, a chemical precursor to a compound of formula A may be used, with or without isolation of a compound of formula A.

In some embodiments, a precursor of a compound of formula A is selected from a compound of formula VI-b:

VI-b wherein:
R² and EWG are as described above for Scheme I and Lg is a suitable leaving group. In some embodiments, such precursors are selected from the group consisting of:

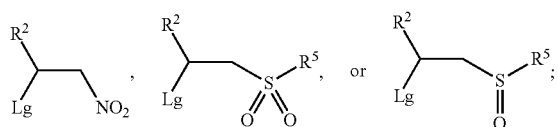

wherein each of R² and R⁵ is as described above and Lg is a suitable leaving group which leaves from parent compound by β-elimination with E2 mechanism under basic conditions to form a double bond as depicted in formula A.

The group "Lg", is a suitable leaving groups, i.e., groups that are readily eliminated when the C—H bond of its β position is weakened by a base. Suitable leaving groups include, but are not limited to, halogen, alkoxy, sulphonyloxy, optionally substituted alkylsulphonyloxy, optionally substituted alkenylsulfonyloxy, optionally substituted arylsulfonyloxy, acyl, and diazonium moieties. Examples of suitable leaving groups include chloro, iodo, bromo, fluoro, acetoxy, methoxy, methanesulfonyloxy (mesyloxy), tosyloxy, trifly-loxy, nitro-phenylsulfonyloxy (nosyloxy), and bromo-phenylsulfonyloxy (brosyloxy).

In certain embodiments, a chemical precursor to a compound of formula B may be used, with or without isolation of a compound of formula B.

In some embodiments, a precursor of a compound of formula B is a compound of formula VII-b:

VII-b wherein:
each of X, R², EWG, and Lg is as described above. In some embodiments, such precursors are selected from the group consisting of:

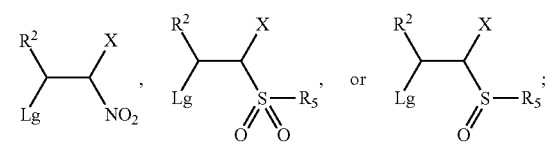

wherein each of X, $R^2$ and $R^5$ is as described above and Lg is a suitable leaving group which leaves from parent compound by β-elimination with E2 mechanism under basic conditions to form a double bond as depicted in formula B.

It will be appreciated that a halogen used in the formation of a compound of formula B may be any halogen that affords formation of a compound of formula B. In some embodiments, a halogen reagent comprises bromine or iodine. In some embodiments, a halogen reagent is $Br_2$ or $I_2$.

In step S-1, the reaction of a compound of formula A with a halogen may employ a suitable solvent. Suitable solvents include polar aprotic solvents (i.e., THF, dioxane, acetonitrile, and combinations thereof), halogenated hydrocarbons (e.g., dichloromethane, chloroform, carbon tetrachloride, methyl chloroform, 1,2-dichloroethane, 1,1-dichloroethane) or halogenated aromatic hydrocarbons (e.g., chlorobenzene, dichlorobenzenes). In some embodiments, a solvent is acetonitrile. In some embodiments, a solvent is dichloromethane.

In some embodiments, a suitable reaction temperature for step S-1 is about −20° C. to about 150° C. In some embodiments, the temperature is about 0° C. to about 85° C. In some embodiments, the temperature is about 35° C. to about 45° C.

Step S-2 utilizes a suitable base in the formation of a compound of formula B. In some embodiments, a suitable base is an inorganic base or an amine base. In some embodiments, a base is triethylamine. In some embodiments, a base is DBU.

Step S-2 may comprise a suitable solvent that may or may not be different than a solvent used in step S-1. Suitable solvents for step S-2 include polar aprotic solvents (i.e., THF, dioxane, acetonitrile, and combinations thereof) or halogenated aromatic hydrocarbons (e.g., chlorobenzene, dichlorobenzenes). In some embodiments, a solvent is acetonitrile. In some embodiments, a solvent is THF.

Suitable reaction temperatures for step S-2 are those that afford the formation of a compound of formula B. In some embodiments, a suitable reaction temperature for step S-2 is about −40° C. to about 60° C. In some embodiments, a suitable reaction temperature for step S-2 is about −10° C. to about 30° C. In some embodiments, a suitable reaction temperature for step S-2 is about −5° C. to about 5° C.

In step S-3, a compound of formula C is reacted with a compound of formula B to form a compound of formula D.

Step S-3 employs a suitable base that may or may not be different from a base used in step S-2. In some embodiments, a suitable base is an inorganic base or an amine base. In some embodiments, a base is DBU. In some embodiments, a base is triethylamine. In some embodiments, a base is a salt (i.e., conjugate base) of a compound of formula C.

Step S-3 may comprise a suitable solvent that may or may not be different than a solvent used in step S-2. Suitable solvents for step S-3 include polar aprotic solvents (i.e., THF, dioxane, acetonitrile, DMSO, DMF, DMA, hexamethylphosphoramide and combinations thereof). In some embodiments, a solvent is acetonitrile. In some embodiments, a solvent is THF.

Suitable reaction temperatures for step S-3 are those that afford the formation of a compound of formula D. In some embodiments, a suitable reaction temperature for step S-3 is about 0° C. to about 150° C. In some embodiments, a suitable reaction temperature for step S-3 is about 40° C. to about 100° C. In some embodiments, a suitable reaction temperature for step S-3 is about 60° C. to about 90° C.

In certain embodiments, each of the aforementioned synthetic steps may be performed sequentially with isolation of each intermediate performed after each step. Alternatively, each of steps S-1, S-2, and S-3, as depicted in Scheme I above, may be performed in a manner whereby no isolation of one or more intermediates A, B, or C is performed.

In certain embodiments, all the steps of the aforementioned synthesis may be performed to prepare the desired final product. In other embodiments, two, three, or more sequential steps may be performed to prepare an intermediate or the desired final product.

Compounds of formula D′, the position 2 unsubstituted naphtho[2,3-b]furan-4,9-dione or naphtho[2,3-b]thiophene-4,9-dione, are parent compounds of formulae II and III as shown in Scheme II. Synthesis of compounds of formula D′ where X is O is described in Scheme I. Synthesis of compounds of formula D′ where X is S is described in US Pat. Publication No. US2006/0142271 (for example, Scheme 2 on page 8), the entire contents of which is hereby incorporated by reference. Synthesis of formulae II and III is carried out as described in the Scheme II.

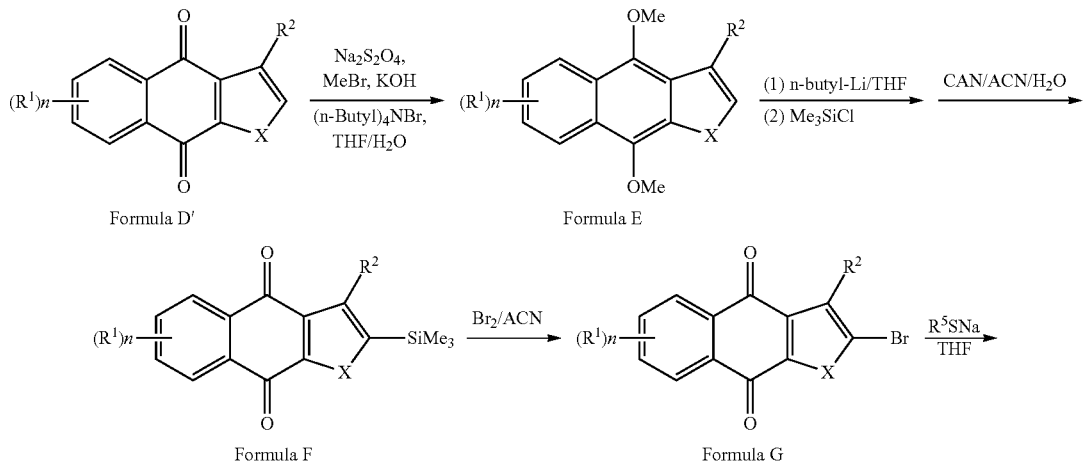

Scheme II:

-continued

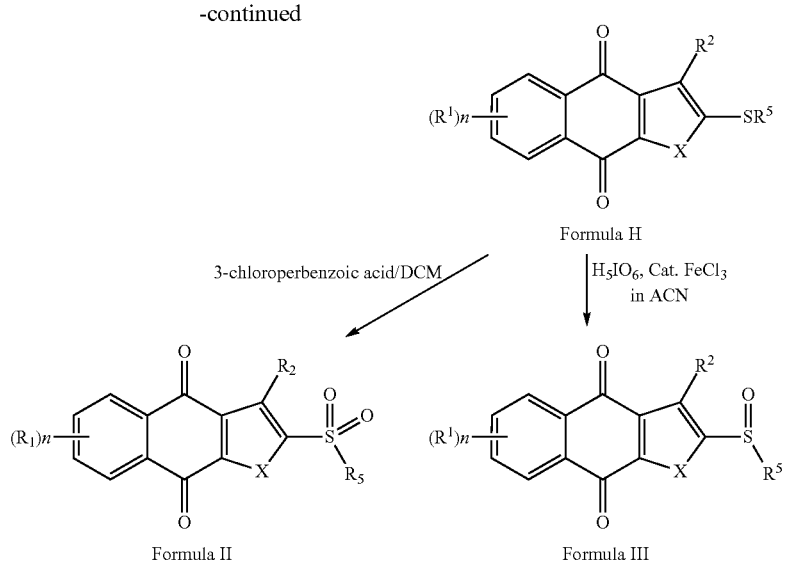

Formula H 3-chloroperbenzoic acid/DCM ↙    ↘ $H_5IO_6$, Cat. $FeCl_3$ in ACN

Formula II    Formula III

In Scheme II, CAN is cerium(IV) ammonium nitrate; cat. is "catalytic"; X is oxygen or sulfur; and DCM, THF, ACN, each of n, $R^1$, $R^2$, $R^5$ is as defined above for Scheme I.

Compounds of formula E, the position 2 unsubstituted 4,9-dimethoxynaphtho[2,3-b]furan or 4,9-dimethoxynaphtho[2,3-b]thiophene, are parent compounds of formulae IV as shown in Scheme III. Synthesis of formulae IV is carried out as described in the Scheme III.

Scheme III:

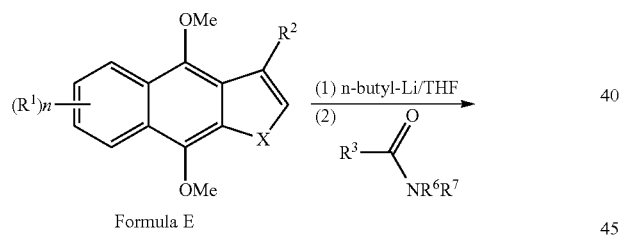

Formula E

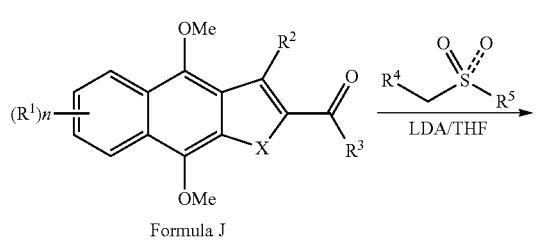

Formula J

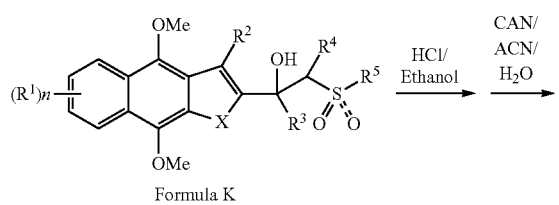

Formula K

-continued

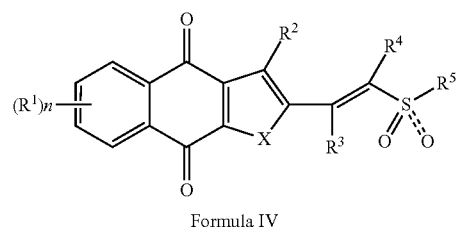

Formula IV

In Scheme III:

LDA is lithium diisopropylamide;

broken line double bond is optionally present;

each of $R^3$ and $R^4$ is independently hydrogen, an optionally substituted group selected from $C_{1-12}$ aliphatic, a 3- to 14-membered carbocycle, a 3- to 14-membered heterocycle, a 6- to 14-membered aryl ring, or a 5- to 14-membered heteroaryl ring;

each of $R^6$ and $R^7$ is independently optionally substituted alkyl or optionally substituted aryl;

and each of n, $R^1$, $R^2$, $R^5$, X, DCM, THF, ACN, are as defined above for Scheme I; CAN is as defined above for Scheme II.

Compounds of formula E, the position 2 unsubstituted 4,9-dimethoxynaphtho[2,3-b]furan or 4,9-dimethoxynaphtho[2,3-b]thiophene, are parent compound of formula IV wherein $R^3$ is hydroxyl as shown in Scheme IV, and are also parent compounds of formula V as shown in Scheme IV. Synthesis of formula IV wherein $R^3$ is hydroxyl together with synthesis of formula V is carried out as described in the Scheme IV.

Scheme IV:

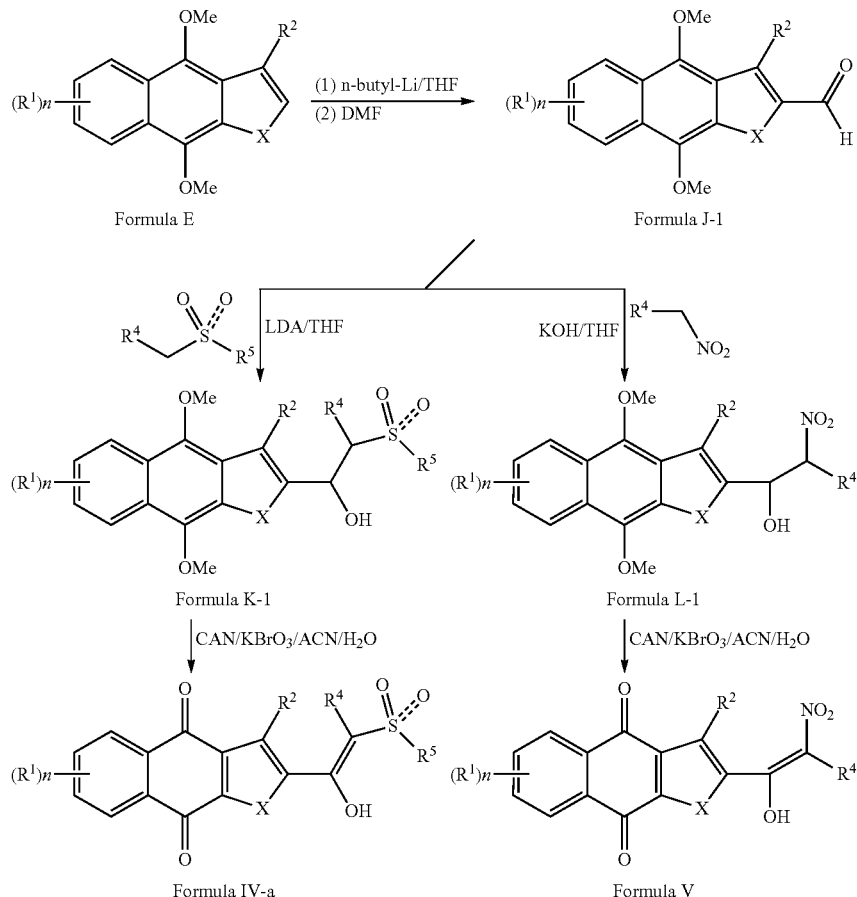

In Scheme IV, $R^4$ and broken line double bond are as defined above for Scheme III; CAN and X are as defined above for Scheme II; each of n, $R^1$, $R^2$, $R^5$, THF, ACN, are as defined above for Scheme I;

Pharmaceutical Compositions

The present invention also provides pharmaceutical compositions comprising a compound of formula I and at least one pharmaceutically acceptable excipient or carrier or diluent.

As used herein, the pharmaceutically acceptable excipient or carrier or diluent is intended to include any and all solvents, dispersion media, coatings, antibacterial and antifungal agents, isotonic and absorption delaying agents, and the like, compatible with pharmaceutical administration. The pharmaceutically acceptable excipient or carrier or diluent including, but not limited to, water, saline solution, dextrose solution, human albumin or its derivative, glycerol mono-(or di-)fatty acid esters, lecithin, phospholipids (such as phosphatidyl choline, phosphatidyl ethanolamine, phosphatidyl inositol, sphingomyelin, and the like), cholesterol, PEG-phospholipids, PEG-cholesterol, PEG-cholesterol derivatives, PEG-vitamin A, PEG-vitamin E, PEG-glycerol mono-(or di-)fatty acid esters, ethylene glycol mono-fatty acid esters, propylene glycol mono-fatty acid esters, 3-dialkyl(C1-8)amino-propylene glycol di-fatty acid esters, poly(ethylene glycol) mono-fatty acid esters, stearic acid, sorbitan esters, polyoxyethylene alkyl ethers, polyoxyethylene castor oil derivatives, polyoxyethylene sorbitan fatty acid esters, polyvinyl alcohol, polyvinylpyrrolidone, poloxamers; poloxamines, mixtures of sucrose stearate and sucrose distearate, random copolymers of vinyl acetate and vinyl pyrrolidone, deoxycholic acid, glycodeoxycholic acid, taurocholic acid, anionic biopolymers (such as casein or its derivative), anionic polymers, cationic biopolymers, salts of these acids (deoxycholic acid, glycocholic acid, glycodeoxycholic acid, taurocholic acid), the bulking agents, and mixtures thereof. The bulking agents includes starches or its derivatives, mannitol, lactose, maltitol, maltodextrin, maltose, dextrates, dextrin, dextrose, fructose, sorbitol, glucose, sucrose, carboxymethylcellulose, hydroxypropylcellulose, microcrystalline cellulose, ethylcellulose, methylcellulose, other suitable cellulose derivatives, gelatin, alginic acid, and its salt, colloidal silicon dioxide, croscarmellose sodium, crospovidone, magnesium aluminum silicate, povidone, benzyl phenylformate, chlorobutanol, diethyl phthalate, calcium stearate, glyceryl palmitostearate, magnesium oxide, poloxamer, polyvinyl alcohol, sodium benzoate, sodium lauryl sulfate, sodium stearyl fumarate, stearic acid, talc, zinc stearate, acacia, acrylic and methacrylic acid co-polymers, gums such as guar gum, milk derivatives such as whey, pharmaceutical glaze, glyceryl palmitostearate, hydrogenated vegetable oil, kaolin, magnesium carbonate, magnesium oxide, polymethacrylates, sodium chloride and mixtures thereof.

Formulations of the compound of Formula I include those suitable for oral, nasal, topical (including buccal and sublingual), rectal, vaginal and/or parenteral administration. The formulation may conveniently be presented in unit dosage form and may be prepared by any methods well known in the art of pharmacy. The amount of active ingredient, which can be combined with a carrier material to produce a single dosage form, will generally be that amount of the compound which produces a therapeutic effect. Generally, out of 100%, this amount will range, for example, from about 1% to about 99% of active ingredient, from about 5% to about 70%, from about 10% to about 30%.

Formulations of the compound of Formula I suitable for oral administration may be in the form of capsules, pills, tablets, cachets, powders, granules, or as a solution or a suspension in an aqueous or non-aqueous or aqueous-organic solvent emulsion liquid, each containing a predetermined amount of a compound of Formula I as an active ingredient.

In solid dosage forms of the compound of Formula I for oral administration, the compound of Formula I at a physical form of crystal, micronized crystal, nanoparticle, or amorphous form is mixed with one or more pharmaceutically acceptable excipient or carrier or diluent, such as glycerol mono-(or di-)fatty acid esters, lecithin, phospholipids (such as phosphatidyl choline, phosphatidyl ethanolamine, phosphatidyl inositol, sphingomyelin, and the like), cholesterol, PEG-phospholipids, PEG-cholesterol, PEG-cholesterol derivatives, PEG-vitamin A, PEG-vitamin E, PEG-glycerol mono-(or di-)fatty acid esters, ethylene glycol mono-fatty acid esters, propylene glycol mono-fatty acid esters, 3-dialkyl(C1-8)amino-propylene glycol di-fatty acid esters, poly(ethylene glycol) mono-fatty acid esters, stearic acid, sorbitan esters, polyoxyethylene alkyl ethers, polyoxyethylene castor oil derivatives, polyoxyethylene sorbitan fatty acid esters, polyvinyl alcohol, polyvinylpyrrolidone, poloxamers; poloxamines, mixtures of sucrose stearate and sucrose distearate, random copolymers of vinyl acetate and vinyl pyrrolidone, deoxycholic acid, glycodeoxycholic acid, taurocholic acid, anionic biopolymers (such as casein or its derivative), anionic polymers, cationic biopolymers, salts of these acids (deoxycholic acid, glycocholic acid, glycodeoxycholic acid, taurocholic acid), bulking agents, and mixtures thereof. Bulking agents includes starches or its derivatives, mannitol, lactose, maltitol, maltodextrin, maltose, dextrates, dextrin, dextrose, fructose, sorbitol, glucose, sucrose, carboxymethylcellulose, hydroxypropylcellulose, microcrystalline cellulose, ethylcellulose, methylcellulose, other suitable cellulose derivatives, gelatin, alginic acid and salts thereof, colloidal silicon dioxide, croscarmellose sodium, crospovidone, magnesium aluminum silicate, povidone, benzyl phenylformate, chlorobutanol, diethyl phthalate, calcium stearate, glyceryl palmitostearate, magnesium oxide, poloxamer, polyvinyl alcohol, sodium benzoate, sodium lauryl sulfate, sodium stearyl fumarate, stearic acid, talc, zinc stearate, acacia, acrylic and methacrylic acid co-polymers, gums such as guar gum, milk derivatives such as whey, pharmaceutical glaze, glyceryl palmitostearate, hydrogenated vegetable oil, kaolin, magnesium carbonate, magnesium oxide, polymethacrylates, sodium chloride and mixtures thereof.

In liquid or semi-liquid dosage forms of the compound of Formula I for oral, nasal, topical, rectal, vaginal and parenteral administration, a compound of Formula I is mixed with one or more pharmaceutically acceptable excipient or carrier or diluent as a solution or a nanoparticle suspension in an aqueous or non-aqueous or aqueous-organic solvent emulsion liquid or semi-liquid, each containing a predetermined amount of a compound of Formula I as an active ingredient. In certain embodiments, pharmaceutically acceptable excipients, carriers, or diluents include, but are not limited to, water, saline solution, dextrose solution, human albumin or its derivative, glycerol mono-(or di-)fatty acid esters, lecithin, phospholipids (such as phosphatidyl choline, phosphatidyl ethanolamine, phosphatidyl inositol, sphingomyelin, and the like), cholesterol, PEG-phospholipids, PEG-cholesterol, PEG-cholesterol derivatives, PEG-vitamin A, PEG-vitamin E, PEG-glycerol mono-(or di-)fatty acid esters, ethylene glycol mono-fatty acid esters, propylene glycol mono-fatty acid esters, 3-dialkyl(C1-8)amino-propylene glycol di-fatty acid esters, poly(ethylene glycol) mono-fatty acid esters, stearic acid, sorbitan esters, polyoxyethylene alkyl ethers, polyoxyethylene castor oil derivatives, polyoxyethylene sorbitan fatty acid esters, polyvinyl alcohol, polyvinylpyrrolidone, poloxamers; poloxamines, mixtures of sucrose stearate and sucrose distearate, random copolymers of vinyl acetate and vinyl pyrrolidone, deoxycholic acid, glycodeoxycholic acid, taurocholic acid, anionic biopolymers (such as casein or its derivative), anionic polymers, cationic biopolymers, salts of these acids (deoxycholic acid, glycocholic acid, glycodeoxycholic acid, taurocholic acid), bulking agents, and mixtures thereof. Bulking agents includes starches or its derivatives, mannitol, lactose, maltitol, maltodextrin, maltose, dextrates, dextrin, dextrose, fructose, sorbitol, glucose, sucrose.

Uses

Compounds of the present invention may be used in vitro or in vivo. In some embodiments, compounds of the present invention are provided for use in medicine. In some embodiments, the present invention provides methods of treating a subject suffering from or susceptible to a disease, disorder, or condition, the method comprising administering to the subject a therapeutically effective amount of a compound of formula I. In certain embodiments, compounds of formula I are useful in the treatment of proliferative diseases. However, inventive compounds described above may also be used in vitro for research or clinical purposes (e.g., determining the susceptibility of a patient's disease to a compound of formula I, researching the mechanism of action, elucidating a cellular pathway or process).

In some embodiments, the present invention provides a method of treating a subject suffering from or susceptible to a proliferative disease, disorder, or condition, the method comprising administering to the subject a therapeutically effective amount of a compound of formula I. In certain embodiments, the proliferative disease is a benign neoplasm. In certain embodiments, the proliferative disease is cancer. In certain embodiments, the proliferative disease is an inflammatory disease. In certain embodiments, the proliferative disease is an autoimmune disease. In certain embodiments, the proliferative disease is diabetic retinopathy.

Compounds of formula I may be used in the treatment of neoplasms. In certain embodiments, the neoplasm is a benign neoplasm. In other embodiments, the neoplasm is a malignant neoplasm.

In some embodiments, the present invention provides a method of treating a subject suffering from or susceptible to cancer, the method comprising administering to the subject a therapeutically effective amount of a compound of formula I. In some embodiments, the cancer is a hematological malignancy. In certain embodiments, the cancer is a solid tumor. Exemplary cancers that may be treated using compounds of formula I include colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, breast cancer, gastric cancer, eye cancer, nasopharyngeal cancer, gallbladder cancer, laryngeal cancer, oral cancer, penile cancer, glandular tumors, rectal cancer, small intestine cancer, head and neck cancer, multiple myeloma, colorectal carcinoma, kaposi sarcoma, ewing's sarcoma, osteosarcoma, leiomyosarcoma, glioma, meningioma, medulloblastoma, melanoma, urethral cancer, vaginal cancer, to name but a few.

In certain embodiments, compounds of formula I are useful for the treatment of diseases, disorders, and conditions of the brain, meninges, and the central nervous system. While not wishing to be bound by any particular theory, it is believed that compounds of formula I are capable of passing through the blood-brain barrier (BBB) and therefore can be useful to treat diseases, disorders, and conditions that require a systemically-administered therapeutic to pass through the BBB.

Hematological malignancies are types of cancers that affect the blood, bone marrow, and/or lymph nodes. Examples of hematological malignancies that may be treated using compounds of formula I include, but are not limited to: acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), Mantle cell lymphoma, B-cell lymphoma, acute lymphoblastic T cell leukemia (T-ALL), acute promyelocytic leukemia, and multiple myeloma.

Compounds of formula I may also be used to treated a refractory or relapsed malignancy. In certain embodiments, the cancer is a refractory and/or relapsed hematological malignancy. For example, the cancer may be resistant to a particular chemotherapeutic agent.

In some embodiments, the present invention provides a method of inhibiting or reducing cancer stem cell survival and/or self renewal with an effective amount of a compound of formula I.

Compounds of formula I may also be used to treat and/or kill cells in vitro or in vivo. In certain embodiments, a cytotoxic concentration of a compound of formula I is contacted with the cells in order to kill them. In some embodiments, a sublethal concentration of a compound of formula I is used to treat the cells. In certain embodiments, the concentration of a compound of formula I ranges from 0.1 nM to 100 µM. In certain embodiments, the concentration of a compound of formula I ranges from 0.01 µM to 100 µM. In certain embodiments, the concentration of a compound of formula I ranges from 0.1 µM to 50 In certain embodiments, the concentration of a compound of formula I ranges from 1 µM to 10 µM. In certain embodiments, the concentration of a compound of formula I ranges from 1 µM to 10 µM, more particularly 1 µM to 5 µM.

Any type of cell may be tested or killed with a compound of formula I. Such cells may be derived from any animal, plant, bacterial, or fungal source, and may be at any stage of differentiation or development. In certain embodiments, cells are animal cells. In certain embodiments, cells are vertebrate cells. In certain embodiments, cells are mammalian cells. In certain embodiments, cells are human cells. Cells may be derived from a male or female human in any stage of development. In certain embodiments, cells are primate cells. In other embodiments, cells are derived from a rodent (e.g., mouse, rat, guinea pig, hamster, gerbil). In certain embodiments, cells are derived from a domesticated animal such as a dog, cat, cow, goat, pig, etc. Cells may also be derived from a genetically engineered animal or plant, such as a transgenic mouse.

Cells used in accordance with the present invention may be wild type or mutant cells, and may be genetically engineered. In certain embodiments, cells are normal cells. In certain embodiments, cells are hematological cells. In certain embodiments, cells are white blood cells. In certain particular embodiments, cells are precursors of white blood cells (e.g., stem cells, progenitor cells, blast cells). In certain embodiments, cells are neoplastic cells. In certain embodiments, cells are cancer cells. In certain embodiments, cells are derived from a hematological malignancy. In other embodiments, cells are derived from a solid tumor. For example, cells may be derived from a patient's tumor (e.g., from a biopsy or surgical excision). In certain embodiments, cells are derived from a blood sample from the subject or from a bone marrow biopsy. In certain embodiments, cells are derived from a lymph node biopsy. Such testing for cytotoxicity may be useful in determining whether a patient will respond to a particular combination therapy. Such testing may also be useful in determining the dosage needed to treat the malignancy. This testing of the susceptibility of a patient's cancer to a compound of formula I would prevent the unnecessary administration of drugs with no effect to the patient. The testing may also allow the use of lower dose of a compound of formula I if the patient's cancer is particularly susceptible to the compound of formula I.

In certain embodiments, cells are derived from cancer cells lines. For example, in certain embodiments, cells are hematopoietic progenitor cells such as $CD34^+$ bone marrow cells. In certain embodiments, cells are A549, DLD1, SW480, LOVO, HT-29, U-20S, MES-SA, SK-MEL-28, Panc-1, DU-145, CNE, U251, Eca-109, MGC80-3, SGC-7901, QGY-7701, BEL-7404, PLC/PRF/5, Huh-7, MOLT-3 (acute lymphoblastic T-cell), SKNLP (neuroblastoma), PC9 (adenocarcinoma), H1650 (adenocarcinoma), H1975 (adenocarcinoma), H2030 (adenocarcinoma), H3255 (adenocarcinoma), TC71 (Ewing's sarcoma), HTP-15 (glioblastoma), A431 (epithelial carcinoma), HeLa (cervical adenocarcinoma), or WD0082 (well-differentiated liposarcoma) cells. In certain embodiments, cell lines are resistant to a particular chemotherapeutic agent.

In some embodiments, the present invention provides a method of treating a subject suffering from or susceptible to obesity or an obesity-related disorder or condition, the method comprising administering to the subject a therapeutically effective amount of a compound of formula I.

In some embodiments, the present invention provides a method of treating a subject suffering from or susceptible to diabetes, the method comprising administering to the subject a therapeutically effective amount of a compound of formula I.

In some embodiments, the present invention provides a method of treating a subject suffering from or susceptible to a metabolic disease, disorder, or condition, the method comprising administering to the subject a therapeutically effective amount of a compound of formula I.

In some embodiments, the present invention provides a method of treating a subject suffering from or susceptible to a degenerative disease, disorder, or condition, the method comprising administering to the subject a therapeutically effective amount of a compound of formula I.

In some embodiments, the present invention provides a method of treating a subject suffering from or susceptible to a disease, disorder, or condition associated with mitochondrial dysfunction, the method comprising administering to the subject a therapeutically effective amount of a compound of formula I.

In some embodiments, the present invention provides a method of treating a subject suffering from or susceptible to a cardiovascular disease, disorder, or condition, the method comprising administering to the subject a therapeutically effective amount of a compound of formula I. In some embodiments, the disease, disorder, or condition is selected from the group consisting of hypertension, congestive heart failure, heart attack, hypertensive heart disease, atherosclerosis, coronary artery disease, angina, ischemia, ischemic stroke.

In some embodiments, compound of formula I may be useful to treat other diseases, disorders, or conditions as described in WO 2009/036059 and WO 2006/088315, the entire contents of each of which are hereby incorporated by reference.

In certain embodiments, compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

In certain embodiments, other therapies or anticancer agents that may be used in combination with the inventive anticancer agents of the present invention include surgery, radiotherapy (γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabine, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Additionally, the present invention also encompasses the use of certain cytotoxic or anticancer agents currently in clinical trials and which may ultimately be approved by the FDA (including, but not limited to, epothilones and analogues thereof and geldanamycins and analogues thereof). For a more comprehensive discussion of updated cancer therapies see The Merck Manual, Eighteenth Ed. 2006, the entire contents of which are hereby incorporated by reference.

In certain embodiments, inventive compounds are useful in treating a subject in clinical remission. In some embodiments, the subject has been treated by surgery and may have limited unresected disease.

If desired, the effective daily dose of the active compound may be administered as two, three, four, five, six, or more sub-doses administered separately at appropriate intervals throughout the day, optionally, in unit dosage forms.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In some embodiments, a chronic treatment involves administering a compound or pharmaceutical composition of the invention repeatedly over the life of the subject. In some embodiments, chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

In certain embodiments, a therapeutically effective amount of a compound of formula I is from about 1 $mg/m^2$ to about 5,000 $mg/m^2$ (I.V.) or from about 1 $mg/m^2$ to about 50,000 $mg/m^2$ (PO). In certain embodiments, a therapeutically effective amount of a compound of formula I is from about 2 $mg/m^2$ to about 3,000 $mg/m^2$ (I.V.) or from about 10 $mg/m^2$ to about 30,000 $mg/m^2$ (PO).

In certain embodiments, a compound of Formula I is administered in a suitable dosage form prepared by combining a therapeutically effective amount of a compound of Formula I with at least one excipient or carrier or diluent listed above according to conventional procedures well known in the art. The dosage form for treatment of cancer may be injected directly into tumors, injected into the blood stream or body cavities or taken orally or applied through the skin with patches.

In certain embodiments, the present invention is directed to prodrugs of compounds of Formula I. The term "prodrug," as used herein, means a compound that is convertible in vivo by metabolic means (e.g. by hydrolysis) to a compound of Formula I. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., Journal of Drug Delivery Reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is hereby incorporated by reference in its entirety.

The invention further provides kits comprising pharmaceutical compositions of an inventive compound. In certain embodiments, such kits include the combination of a compound of the present invention and another chemotherapeutic agent. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. The kit may include a full cycle of chemotherapy. In certain embodiments, the kit includes multiple cycles of chemotherapy.

EXEMPLIFICATION

Example 1

Preparation of
2-hydroxy-7-chloro-1,4-naphthoquinone

To the solution of 10 grams (60 mmoles) of 5-chloro-1-indanone in 200 mL of ethyl ether cooled in ice-bath, 66 mL (66 mmoles) of 1 M methylmagnesium chloride in ethyl ether was dropped slowly over 30 minutes. The reaction mixture was stirred at room temperature for 3 hours, and then evaporated to sticky residue. To the residue, 150 mL of 2N hydrochloric acid in ethanol/water (1:1) was added, and the resulting mixture was refluxed for 1 hour. After cooling down, the mixture was extracted with dichloromethane twice, and the combined organic phase was washed with water and dried with anhydrous sodium sulfate. The intermediate product 3-methyl-6-chloroindene was purified with silica gel chromatograph using hexane/dichloromethane (4:1) as elution solvent.

To a vigorously stirred solution of 18 grams of sodium dichromate hydrate and 1 gram of sodium benzene sulfonate in 300 mL of sulfuric acid/water (1:5) at 55° C., 7.5 grams (46 mmoles) of 3-methyl-6-chloroindene was added dropwise in 1 hour. The reaction mixture was further stirred for 30 minutes at 55° C. After chilling overnight at 0° C., the mixture was filtered, and the solid was washed successively with cold water and benzene and dried under vacuum.

The crude intermediate product (5-chloro-2-acetyl)phenylacetic acid was dissolved in the mixture of 100 mL of anhydrous ethanol and 10 mL of sulfuric acid. Then the resulting mixture was stirred for 48 hours at room temperature. After dilution with 300 mL of water, the mixture was extracted with dichloromethane twice. The combined organic phase was washed with water and dried with anhydrous sodium sulfate. The intermediate product ethyl (5-chloro-2-acetyl)phenylacetate was purified with silica gel chromatograph using dichloromethane/ethyl acetate (4:1) as elution solvent.

1.15 gram (50 mmoles) of sodium metal was suspended in 150 mL of anhydrous ethanol with vigorous stirring. After the sodium metal disappeared, 6 grams (25 mmoles) of ethyl (5-chloro-2-acetyl)phenylacetate was added, and the resulting mixture was stirred at room temperature in an open flask for 24 hours. The mixture was chilled to 0° C. and filtered, and the obtained brick red solid was washed with cold ethanol, and then dissolved in 500 mL of water. To the red aqueous solution with vigorous stirring, 1N hydrochloric acid was added dropwise until the solution turned to yellow. The yellow solid was filtered, washed with water and dried under vacuum. 3.2 grams of 2-hydroxy-7-chloro-1,4-naphthoquinone was obtained (overall yield 25.6%) and used without characterization Example 2

Preparation of naphtho[2,3-b]furan-4,9-dione

To the solution of 5 grams (47.2 mmoles) of methyl vinyl sulfone in 100 mL of dichloromethane, 7.9 grams (49.5 mmoles) of bromine was added. The mixture was refluxed for 6 hours, and then evaporated to sticky residue. To the residue solution in 150 mL of tetrahydrofitran cooled in ice bath, 7.5 grams (49.5 mmoles) of 1,8-Diazabicyclo[5.4.0]undec-7-ene (DBU) was dropped slowly over 20 minutes while stirring vigorously. The reaction mixture was further stirred for 30 minutes in ice bath, then 8.2 grams (47.2 mmoles) of 2-hydroxy-1,4-naphthoquinone and 7.5 grams (49.5 mmoles) of 1,8-Diazabicyclo[5.4.0]undec-7-ene (DBU) were added. The mixture was reflux for 6 hours, and then evaporated to sticky residue. The residue was dissolved in 300 mL of dichloromethane, and washed with 300 mL of water, 300 mL of 2% aqueous citric acid solution, successively, and dried with 30 grams of anhydrous sodium sulfate. The naphtho[2,3-b]furan-4,9-dione product was purified with silica gel column using dichloromethane/hexane (3:1) as elution solvent. 2.3 grams of product (overall yield 25%) was obtained and characterized by $^1$H NMR and mass spectrum. $^1$H NMR (in DMSO) δ 7.17 (d, J=2, 1H), 7.86-7.91 (m, 2H), 8.09-8.13 (m, 2H), 8.32 (d, J=2.1 H). Mass (M+H) is 199.

Example 3

Preparation of
3-phenyl-naphtho[2,3-b]furan-4,9-dione

To the solution of 5 grams (33.5 mmoles) of [(E)-2-nitroethenyl]benzene in 100 mL of dichloromethane, 5.6 grams (35.2 mmoles) of bromine was added. The mixture was refluxed for 12 hours, and then evaporated to dryness. To the residue solution in 150 mL of tetrahydrofuran cooled in ice bath, 5.3 grams (35.2 mmoles) of 1,8-Diazabicyclo[5.4.0] undec-7-ene (DBU) was dropped slowly over 20 minutes while stirring vigorously. The reaction mixture was further stirred for 30 minutes in ice bath, then 5.8 grams (33.5 mmoles) of 2-hydroxy-1,4-naphthoquinone and 5.3 grams (35.2 mmoles) of 1,8-Diazabicyclo[5.4.0]undec-7-ene (DBU) were added. The mixture was reflux for 3 hours, and then evaporated to sticky residue. The residue was dissolved in 300 mL of dichloromethane, and washed with 300 mL of water, 300 mL of 2% aqueous citric acid solution, successively, and dried with 30 grams of anhydrous sodium sulfate. The 3-phenyl-naphtho[2,3-b]furan-4,9-dione product was purified with silica gel column using dichloromethane/hexane (3:1) as elution solvent. 6.4 grams of product (overall yield 70%) was obtained and characterized by $^1$H NMR and mass spectrum. $^1$H NMR (in DMSO) δ 7.44-7.52 (m, 3H), 7.77-7.79 (m, 2H), 7.89-7.93 (m, 2H), 8.10-8.15 (m, 2H), 8.58 (s, 1H). Mass (M+H) is 275.

Example 4

Preparation of 7-chloro-naphtho[2,3-b]furan-4,9-dione 0.77 gram (3.3 mmoles) of 7-chloro-naphtho[2,3-b]furan-4,9-dione was obtained from 1.52 gram (14.3 mmoles) of methyl vinyl sulfone and 3 grams (14.3 mmoles) of 2-hydroxy-7-chloro-1,4-naphthoquinone by using the procedure described in Example 2 with overall yield 23.0%. $^1$H NMR (in CDCl$_3$) δ 7.04 (d, J=2, 1H), 7.74 (q, J1=2, J2=8, 1H), 7.82 (d, J=2, 1H), 8.17 (d, J=8.1H), 8.21 (d, J=2, 1H).

Example 5

Preparation of 4,9-dimethoxy-naphtho[2,3-b]furan

To the solution of 2 grams (10.1 mmoles) of naphtho[2,3-b]furan-4,9-dione in 150 mL of tetrahydrofuran/water (2:1), 7.03 grams (40.4 mmoles) of sodium hydrosulfite, 0.81 gram (20.2 mmoles) of sodium hydroxide, 0.64 gram (2 mmoles) of tetrabutylammonium bromide and 3.84 grams (40.4 mmoles) of methyl bromide were added at once. The mixture was stirred in a sealed round-bottom flask at room temperature for 4 hours, and then evaporated to remove tetrahydrofuran. The remaining aqueous solution was extracted with dichloromethane twice. The combined organic phase was washed with water, dried with anhydrous sodium sulfate, and evaporated to dryness. The product in the residue was purified with silica gel column using dichloromethane/hexane (2:1) as elution solvent. 1.8 grams of product (yield 80%) was obtained and characterized by $^1$H NMR and mass spectrum. $^1$H NMR (in CDCl$_3$) δ 4.20 (s, 3H), 4.30 (s, 3H), 7.06 (d, J=2, 1H), 7.45-7.53 (m, 2H), 7.67 (d, J=2, 1H), 8.26-8.32 (m, 2H). Mass (M+H) is 229.

Example 6

Preparation of 3-phenyl-4,9-dimethoxy-naphtho[2,3-b]furan

To the solution of 4 grams (14.6 mmoles) of 3-phenyl-naphtho[2,3-b]furan-4,9-dione in 150 mL of tetrahydrofuran/water (2:1), 10.2 grams (58.4 mmoles) of sodium hydrosulfite, 1.2 gram (29.2 mmoles) of sodium hydroxide, 0.96 gram (3 mmoles) of tetrabutylammonium bromide and 5.5 grams (58.4 mmoles) of methyl bromide were added. The mixture was stirred in a sealed round-bottom flask at room temperature for 4 hours, and then evaporated to remove tetrahydrofuran. The remaining aqueous solution was extracted with dichloromethane twice. The combined organic phase was washed with water, dried with anhydrous sodium sulfate, and evaporated to dryness. The product in the residue was purified with silica gel column using dichloromethane/hexane (2:1) as elution solvent. 3.6 grams of product (yield 80%) was obtained and characterized by $^1$H NMR and mass spectrum. $^1$H NMR (in CDCl$_3$) δ 3.48 (s, 3H), 4.34 (s, 3H), 7.44-7.53 (m, 5H), 7.73 (s, 1H), 7.77-7.79 (m, 2H), 8.25-8.36 (m, 2H). Mass (M+H) is 305.

Example 7

Preparation of 7-chloro-4,9-dimethoxy-naphtho[2,3-b]furan 0.7 gram (2.67 mmoles) of 7-chloro-4,9-dimethoxy-naphtho[2,3-b]furan was obtained from 0.75 gram (3.23 mmoles) of 7-chloro-naphtho[2,3-b]furan-4,9-dione by using the procedure described in Examples 5 and 6 with overall yield 82.8%. $^1$H NMR (in CDCl$_3$) δ 4.17 (s, 3H), 4.26 (s, 3H), 7.05 (d, J=2, 1H), 7.35 (q, J1=2, J2=8, 1H), 7.66 (d, J=2, 1H), 8.18 (d, J=8.1H), 8.24 (d, J=2, 1H).

Example 8

Preparation of 2-trimethylsilyl-naphtho[2,3-b]furan-4,9-dione

To the solution of 4 mL 2.2 M n-butyl lithium diluted with 20 mL of anhydrous tetrahydrofuran in an ice bath, 1 gram (4.4 mmoles) of 4,9-dimethoxy-naphtho[2,3-b]furan in 20 mL of anhydrous tetrahydrofuran was added dropwise over 5 minutes. The mixture was further stirred for 30 minutes in ice bath, and then 0.95 gram (8.8 mmoles) of chlorotrimethylsilane was added dropwise over 5 minutes. The mixture was stirred for additional 20 minutes in ice bath, and then further stirred for 30 minutes at room temperature. The reaction mixture was stopped by addition of 100 mL 0.1N hydrochloric acid, and then evaporated to remove tetrahydrofuran. The remaining aqueous solution was extracted with dichloromethane twice. The combined organic phase was washed with water, dried with anhydrous sodium sulfate, and evaporated to dryness. The 1.2 gram (4 mmoles) of crude product 2-trimethylsilyl-4,9-dimethoxy-naphtho[2,3-b]furan was obtained, and was used for next step reaction without purification.

To 1.2 gram (4 mmoles) of crude product 2-trimethylsilyl-4,9-dimethoxy-naphtho[2,3-b]furan in 50 mL of acetonitrile/water (4:1) in ice bath, 4.8 grams (8.7 mmoles) of cerium ammonium nitrate (CAN) solution in 50 mL of acetonitrile/water (1:4) was added dropwise over 10 minutes. The mixture was further stirred in ice bath for 1 hour, and then evaporated to remove acetonitrile. The remaining aqueous suspension was filtered, and the collected solid was washed with water and crystallized in ethanol/water. Pure crystal product was filtered and dried under vacuum. 0.89 grams of product (overall yield 75%) was obtained and characterized by $^1$H NMR and mass spectrum. $^1$H NMR (in CDCl$_3$) δ 0.41 (s, 9H), 7.16 (s, 1H), 7.75-7.78 (m, 2H), 8.19-8.26 (m, 2H). Mass (M+H) is 271.

Example 9

Preparation of 2-trimethylsilyl-3-phenyl-naphtho[2,3-b]furan-4,9-dione 1.7 gram (4.95 mmoles) of 2-trimethylsilyl-3-phenyl-naphtho[2,3-b]furan-4,9-dione was obtained from 2 grams (6.6 mmoles) of 3-phenyl-4,9-dimethoxy-naphtho[2,3-b]furan by using the procedure described in Example 8 with overall yield 75.0%. Product was characterized by $^1$H NMR and mass spectrum. $^1$H NMR (in DMSO) δ 0.18 (s, 9H), 7.41-7.50 (m, 5H), 7.83-7.89 (m, 2H), 7.97-8.01 (m, 1H), 8.10-8.13 (m, 1H). Mass (M+H) is 347.

Example 10

Preparation of 2-bromo-naphtho[2,3-b]furan-4,9-dione

To the solution of 0.8 gram (3.0 mmoles) of 2-trimethylsilyl-naphtho[2,3-b]furan-4,9-dione in 20 mL of acetonitrile at room temperature, 0.53 grams (3.3 mmoles) of bromine in 20 mL of acetonitrile was added dropwise over 5 minutes. The mixture was further stirred for 30 minutes at room temperature, and then evaporated to dryness. The residue was crystallized in ethanol/water. Pure crystal product was filtered and dried under vacuum. 0.75 grams of product (yield 90%) was obtained and characterized by $^1$H NMR and mass spectrum. $^1$H NMR (in CDCl$_3$) δ 6.96 (s, 1H), 7.76-7.82 (m, 2H), 8.18-8.25 (m, 2H). Mass (M+H) is 277 and 279.

Example 11

Preparation of 2-bromo-3-phenyl-naphtho[2,3-b]furan-4,9-dione 1.5 gram (4.16 mmoles) of 2-bromo-3-phenyl-naphtho[2,3-b]furan-4,9-dione was obtained from 1.6 gram (4.62 mmoles) of 2-trimethylsilyl-3-phenyl-naphtho[2,3-b]furan-4,9-dione by using the procedure described in Example 10 with overall yield 90%. Product was characterized by $^1$H NMR and mass spectrum. $^1$H NMR (in DMSO) δ 7.47-7.59 (m, 5H), 7.88-7.93 (m, 2H), 8.02-8.06 (m, 1H), 8.12-8.14 (m, 1H). Mass (M+H) is 353 and 355.

Example 12

Preparation of 2-methylthio-naphtho[2,3-b]furan-4,9-dione

To the solution of 0.7 gram (2.5 mmoles) of 2-bromo-naphtho[2,3-b]furan-4,9-dione in 20 mL of tetrahydrofuran at room temperature, 0.4 grams (5.0 mmoles) of MeSNa in 5 mL of water was added dropwise over 1 minute. The mixture was further stirred for 2 hours at room temperature, and then evaporated to remove tetrahydrofuran. To the residue, 20 mL of 1N hydrochloric acid was added, and the resulting mixture was filtered. The solid was washed with water, and then crystallized in ethanol/water. Pure crystal product was filtered and dried under vacuum. 0.55 grams of product (yield 90%) was obtained and characterized by $^1$H NMR and mass spectrum. $^1$H NMR (in CDCl$_3$) δ 2.66 (s, 3H), 6.79 (s, 1H), 7.75-7.79 (m, 2H), 8.18-8.25 (m, 2H). Mass (M+H) is 245.

Example 13

Preparation of 2-methylthio-3-phenyl-naphtho[2,3-b]furan-4,9-dione 1.14 gram (3.57 mmoles) of 2-methylthio-3-phenyl-naphtho[2,3-b]furan-4,9-dione was obtained from 1.4 gram (3.97 mmoles) of 2-bromo-3-phenyl-naphtho[2,3-b]furan-4,9-dione using the procedure described in Example 12 with overall yield 90%. Product was characterized by $^1$H NMR and mass spectrum. $^1$H NMR (in DMSO) δ 2.62 (s, 3H), 7.45-7.55 (m, 5H), 7.87-7.90 (m, 2H), 8.03-8.05 (m, 1H), 8.12-8.14 (m, 1H). Mass (M+H) is 321.

Example 14

Preparation of 2-methylsulfonyl-naphtho[2,3-b]furan-4,9-dione (compound I)

To a solution of 0.5 gram (2.05 mmoles) of 2-methylthio-naphtho[2,3-b]furan-4,9-dione in 30 mL of dichloromethane in ice bath, 0.57 grams (2.46 mmoles) of 70% purity 3-chloroperbenzoic acid was added. The mixture was stirred in ice bath for 30 minutes, further stirred for 2 hours at room temperature, then diluted with 100 mL of dichloromethane and washed with 150 mL of 5% sodium bicarbonate twice. The organic phase was dried with anhydrous sodium sulfate, and evaporated to dryness. The residue was crystallized in ethanol/water. 0.48 grams of product (yield 85%) was obtained and characterized by $^1$H NMR and mass spectrum. $^1$H NMR (in CDCl$_3$) δ 3.34 (s, 1H), 7.68 (s, 1H), 7.85-7.87 (m, 2H), 8.26-8.30 (m, 2H). Mass (M+H) is 277.

Example 15

Preparation of 2-methylsulfinyl-naphtho[2,3-b]furan-4,9-dione (compound II)

To a solution of 0.5 gram (2.05 mmoles) of 2-methylthio-naphtho[2,3-b]furan-4,9-dione in 20 mL of acetonitrile at room temperature, 0.49 grams (2.15 mmoles) of periodic acid followed by 2 mg of ferric chloride was added. The mixture was stirred for 10 minutes at room temperature, then 50 mL of water was added, and the resulting mixture was evaporated to remove acetonitrile. The remaining aqueous suspension was filtered, and the obtained solid was washed with water and dried under vacuum. The crude solid product was purified with silica gel chromatograph using dichloromethane/ethyl acetate (9:1) as elution solvent. 0.43 grams of product (yield 80%) was obtained and characterized by $^1$H NMR and mass spectrum. $^1$H NMR (in DMSO) δ 3.14 (s, 3H), 7.81 (s, 1H), 7.92-7.94 (m, 2H), 8.12-8.17 (m, 2H). Mass (M+H) is 261.

Example 16

Preparation of 2-methylsulfonyl-3-phenyl-naphtho[2,3-b]furan-4,9-dione (compound XV)

0.38 gram (1.08 mmoles) of 2-methylsulfonyl-3-phenyl-naphtho[2,3-b]furan-4,9-dione (compound XV) was obtained from 0.41 gram (1.27 mmoles) of 2-methylthio-3-phenyl-naphtho[2,3-b]furan-4,9-dione by using the procedure described in Example 14 with yield of 85%. Product was characterized by $^1$H NMR and mass spectrum. $^1$H NMR (in DMSO) δ 3.41 (s, 1H), 7.50-7.57 (m, 5H), 7.92-7.94 (m, 2H), 8.03-8.06 (m, 1H), 8.16-8.19 (m, 1H). Mass (M+H) is 353.

Example 17

Preparation of 2-methylsulfinyl-3-phenyl-naphtho[2,3-b]furan-4,9-dione (compound XVI)

0.48 gram (1.43 mmoles) of 2-methylsulfinyl-3-phenyl-naphtho[2,3-b]furan-4,9-dione (compound XVI) was obtained from 0.57 gram (1.79 mmoles) of 2-methylthio-3-phenyl-naphtho[2,3-b]furan-4,9-dione using the procedure described in Example 15 with overall yield 80%. Product was characterized by $^1$H NMR and mass spectrum. $^1$H NMR (in CDCl$_3$) δ 3.18 (s, 3H), 7.54-7.56 (m, 3H), 7.63-7.66 (m, 2H), 7.82-7.84 (m, 2H), 8.18-8.20 (m, 1H), 8.28-8.30 (m, 1H). Mass (M+H) is 337.

Example 18

Preparation of 2-oxo-4,9-dimethoxy-naphtho[2,3-b]furan

To a solution of 5.5 mL (12.28 mmoles) of 2.2 M n-butyl lithium diluted with 20 mL of anhydrous tetrahydrofuran in an ice bath, 1.4 gram (6.14 mmoles) of 4,9-dimethoxy-naphtho[2,3-b]furan in 20 mL of anhydrous tetrahydrofuran was added dropwise over 5 minutes. The mixture was further stirred for 40 minutes in ice bath, and then 0.95 mL (12.28 mmoles) of N,N-dimethylformamide was added dropwise over 5 minutes. The mixture was stirred for additional 30 minutes in ice bath, and then further stirred for 120 minutes at room temperature. The reaction mixture was stopped by addition of 100 mL 0.1N hydrochloric acid, and then evaporated to remove tetrahydrofuran. The remaining aqueous solution was extracted with dichloromethane twice. The combined organic phase was washed with water, dried with anhydrous sodium sulfate, and evaporated to dryness. Product was purified by silica gel chromatograph using dichloromethane as elution solvent. 1.20 gram (4.69 mmoles) of product was obtained with yield of 76% and characterized by $^1$H NMR and mass spectrum. $^1$H NMR (in CDCl$_3$) δ 4.30 (s, 3H), 4.34 (s, 3H), 7.47-7.51 (m, 1H), 7.55-7.59 (m, 1H), 7.89 (s, 1H), 8.29-8.33 (m, 2H), 9.95 (s, 1H). Mass (M+H) is 257.

Example 19

Preparation of 2-acetyl-4,9-dimethoxy-naphtho[2,3-b]furan 0.83 gram (3.08 mmoles) of 2-acetyl-4,9-dimethoxy-naphtho[2,3-b]furan was obtained from 1 gram (4.4 mmoles) of 4,9-dimethoxy-naphtho[2,3-b]furan and 0.77 gram (8.8 mmoles) of N,N-dimethylacetamide using the procedure described in Example 18 with yield of 70% and characterized by $^1$H NMR and mass spectrum. $^1$H NMR (in CDCl$_3$) δ 2.71 (s, 3H), 4.27 (s, 3H), 4.34 (s, 3H), 7.46-7.50 (m, 1H), 7.53-7.57 (m, 1H), 7.83 (s, 1H), 8.28-8.32 (m, 2H). Mass (M+H) is 271.

Example 20

Preparation of 2-(1-hydroxyl-2-methylsulfonyl-ethenyl)-naphtho[2,3-b]furan-4,9-dione (Compound XX)

To a solution of 0.62 mL (4.4 mmoles) of diisopropylamine in 10 mL of anhydrous tetrahydrofuran in an ice bath, 2 mL of 2.2 M n-butyl lithium was added. The mixture was stirred in an ice bath for 10 minutes, then 0.36 mL (4.4 mmoles) of dimethyl sulfone was added. After further stirred in an ice bath for 10 minutes, 1 gram (3.9 mmoles) of 2-oxo-4,9-dimethoxy-naphtho[2,3-b]furan in 20 mL of anhydrous tetrahydrofuran was added dropwise over 5 minutes to the mixture. The resulting mixture was further stirred for 90 minutes at room temperature, then 100 mL of 0.1N hydrochloric acid was added to stop reaction. The reaction mixture was evaporated to remove tetrahydrofuran, and remaining aqueous solution was extracted with dichloromethane twice. The combined organic phase was washed with water, dried with anhydrous sodium sulfate, and evaporated to dryness. The crude product was directly used for next step reaction without purification.

To a solution of crude 2-(1-hydroxyl-2-methylsulfonyl-ethyl)-4,9-dimethoxy-naphtho[2,3-b]furan from previous step in 40 mL of acetonitrile/water (4:1) in an ice bath, a solution of 4.4 grams (8 mmoles) of cerium ammonium nitrate and 1.34 gram (8 mmoles) of potassium bromated in 40 mL of acetonitrile/water (1:4) was added dropwise over 20 minutes. The resulting mixture was further stirred for 120 minutes in an ice bath, and then was evaporated to remove acetonitrile. The remaining aqueous solution was extracted with dichloromethane twice. The combined organic phase was washed with water, dried with anhydrous sodium sulfate, and evaporated to dryness. The residue was subjected to silica gel chromatograph purification using dichloromethane/ethyl acetate (4:1) as elution solvent. 0.64 gram (2 mmoles) of product was obtained with overall yield of 51% and characterized by $^1$H NMR and mass spectrum. $^1$H NMR (in CDCl$_3$) δ 3.20 (s, 3H), 4.68 (s, 2H), 7.84-7.87 (m, 3H), 8.23-8.33 (m, 2H). Mass (M+H) is 319.

Example 21

Biological Assays

In vitro anticancer activity of the compound of Formula I was performed using popular MTT method (Archives of Biochemistry and Biophysics, 1993, 303, 2474-82) against lung cancer, colorectal cancer, cervical cancer, osteosarcoma, leiomyosarcoma, malignant melanoma, pancreas cancer, prostate cancer, nasopharyngeal cancer, glioma, esophageal cancer, stomach cancer, and liver cancer.

Cell Culture: A549, DLD1, SW480, LOVO, HT-29, Hela, U-20S, MES-SA, SK-MEL-28, Panc-1, DU-145, CNE, U251, Eca-109, MGC80-3, QGY-7701, BEL-7404, PLC/PRF/5, Huh-7, and SGC-7901 cells were maintained in Dulbecco's Modified Eagle Medium (DMEM) (imported from Invitrogen, Carlsbad, Calif., USA) supplemented with 10% fetal bovine serum (FBS) (Si Ji Qing, Hangzhou, China) and 1% penicillin/streptomycin/amphotercin B (imported from Invitrogen, Carlsbad, Calif., USA).

Cell Viability Determination: Popular MTT method (Archives of Biochemistry and Biophysics. 1993, 303, 474-482) was used to screen the in vitro effects of the invented drugs. Briefly, 5000 to 10000 cells were inoculated per well in a 96-well plate. After overnight incubation, drug was added to the wells at final concentration of 10 μM, 5 μM, 2.5 μM, 1.25 μM, or 1 μM, 0.75 μM, 0.5 μM and 0.25 μM in complete culture medium. Each dose level covered 4 equivalent wells. After 48 hour incubation, one tenth volume of 5 mg/mL MTT (thiazolyl blue tetrazolium bromide, Sigma-Aldrich) stock solution was added, and incubation continued for 2 hours. Then medium was removed and 100 μL of isopropanol solution comprising 86% isopropanol, 4% aqueous 1N HCl and 10% aqueous solution of 10% SDS was added. The absorbance of each well at 570 nm wavelength was measured by a micro-plate reader after gentle shaking for 20 minutes. Drug concentrations of 50% cell viability (IC$_{50}$) were calculated by LOGIT method.

TABLE 2

| | Drug concentrations for 50% cell viability (IC50, μM). | | | | |
|---|---|---|---|---|---|
| Type of Cancer | Name of Cell line | Compound I | Compound II | Compound XV | Compound XVI |
| lung cancer | A549 | 2.50 | 2.50 | >10 | 6.89 |
| colorectal cancer | DLD1 | 0.29 | 0.28 | 2.51 | 1.00 |
| | SW480 | 1.17 | 1.25 | n/a [1] | n/a |

TABLE 2-continued

Drug concentrations for 50% cell viability (IC50, μM).

| Type of Cancer | Name of Cell line | Compound I | Compound II | Compound XV | Compound XVI |
|---|---|---|---|---|---|
| | LOVO | 2.15 | 4.57 | n/a | n/a |
| | HT-29 | 0.72 | 0.78 | n/a | n/a |
| cervical cancer | Hela | 1.20 | 1.49 | n/a | n/a |
| osteosarcoma | U-20S | 0.43 | 0.39 | 3.61 | 1.25 |
| leiomyosarcoma | MES-SA | 1.20 | 1.00 | n/a | n/a |
| malignant melanoma | SK-MEL-28 | 0.22 | 0.24 | n/a | n/a |
| pancreatic cancer | Panc-1 | 1.60 | 1.25 | n/a | n/a |
| prostate cancer | DU-145 | 0.43 | 0.50 | 5.00 | 3.20 |
| nasopharyngeal cancer | CNE | 1.36 | 1.25 | n/a | n/a |
| glioma | U251 | 1.00 | 1.00 | n/a | n/a |
| esophageal cancer | Eca-109 | 3.45 | 3.80 | n/a | n/a |
| stomach cancer | MGC80-3 | 1.20 | 1.20 | n/a | n/a |
| | SGC-7901 | 2.50 | 2.50 | | |
| liver cancer | QGY-7701 | 3.50 | 2.5 | n/a | n/a |
| | BEL-7404 | 1.11 | 1.10 | n/a | n/a |
| | PLC/PRF/5 | 2.50 | 2.00 | n/a | n/a |
| | Huh-7 | 2.50 | 2.50 | n/a | n/a |

[1] n/a = Not tested.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

INCORPORATION OF REFERENCES

All publications and patent documents cited in this application are incorporated by reference in their entirety to the same extent as if the contents of each individual publication or patent document were incorporated herein.

What is claimed is:
1. A compound of formula I:

I or a pharmaceutically acceptable salt thereof;
wherein:
  n is 0-4;
  m is 0-2;
  X is O or S;
  each $R^1$ is independently halogen; —$NO_2$; —CN; —OR; —SR; —$N^+(R)_3$; —$N(R)_2$; —C(O)R; —$CO_2$R; —C(O)C(O)R; —C(O)$CH_2$C(O)R; —S(O)R; —$S(O)_2$R; —C(O)$N(R)_2$; —$SO_2N(R)_2$; —OC(O)R; —N(R)C(O)R; —N(R)$N(R)_2$; —N(R)C(=NR)$N(R)_2$; —C(=NR)$N(R)_2$; —C=NOR; —N(R)C(O)$N(R)_2$; —N(R)$SO_2$N$(R)_2$; —N(R)$SO_2$R; —OC(O)$N(R)_2$; or an optionally substituted group selected from $C_{1-12}$ aliphatic; a 3- to 14-membered carbocycle; a 3- to 14-membered heterocycle; a 6- to 14-membered aryl ring; or a 5- to 14-membered heteroaryl ring, or:

two $R^1$ groups on adjacent carbon atoms are taken together with their intervening atoms to form an optionally substituted ring selected from 3- to 14-membered carbocycle; 3- to 14-membered heterocycle; a 6- to 14-membered aryl ring; or a 5- to 14-membered heteroaryl ring;

each $R^2$, $R^3$, and $R^4$ is independently hydrogen; halogen; —$NO_2$; —CN; —OR; —SR; —$N^+(R)_3$; —$N(R)_2$; —C(O)R; —$CO_2$R; —C(O)C(O)R; —C(O)$CH_2$C(O)R; —S(O)R; —$S(O)_2$R; —C(O)$N(R)_2$; —$SO_2N(R)_2$; —OC(O)R; —N(R)C(O)R; —N(R)$N(R)_2$; —N(R)C(=NR)$N(R)_2$; —C(=NR)$N(R)_2$; —C=NOR; —N(R)C(O)$N(R)_2$; —N(R)$SO_2N(R)_2$; —N(R)$SO_2$R; —OC(O)$N(R)_2$; or an optionally substituted group selected from $C_{1-12}$ aliphatic; a 3- to 14-membered carbocycle; a 3- to 14-membered heterocycle; a 6- to 14-membered aryl ring; or a 5- to 14-membered heteroaryl ring;

R' is —$S(O)R^5$; —$S(O)_2R^5$; or —$NO_2$, wherein when m is O, R' is —$S(O)R^5$ or —$S(O)_2R^5$;

$R^5$ is —OR; —SR; —$N(R)_2$; or an optionally substituted group selected from $C_{1-12}$ aliphatic; a 3- to 14-membered carbocycle; a 3- to 14-membered heterocycle; a 6- to 14-membered aryl ring; or a 5- to 14-membered heteroaryl ring; and each R is independently hydrogen or an optionally substituted group selected from $C_{1-12}$ aliphatic; a 3- to 14-membered carbocycle; a 3- to 14-membered heterocycle; a 6- to 14-membered aryl ring; or a 5- to 14-membered heteroaryl ring;

wherein when m is 1 or 2, each double bond independently has Z or E stereochemistry;

Provided that either $R^3$ or $R^4$ is not hydrogen when R' is —$NO_2$;

Further provided that $R^2$ is not methyl when R' is —$S(O)_2$OH.

2. The compound of claim 1, wherein n is 0.
3. The compound of claim 1, wherein n is 1.
4. The compound of claim 1, wherein m is 0.
5. The compound of claim 1, wherein m is 1.
6. The compound of claim 1, wherein m is 2.
7. The compound of claim 1, wherein $R^1$ is halogen.
8. The compound of claim 1, wherein $R^2$ is hydrogen.
9. The compound of claim 1, wherein $R^2$ is optionally substituted amine.
10. The compound of claim 1, wherein $R^3$ is hydrogen.

11. The compound of claim 1, wherein $R^3$ is hydroxyl.

12. The compound of claim 1, wherein $R^4$ is hydrogen.

13. The compound of claim 1, wherein R' is —S(O)$R^5$.

14. The compound of claim 1, wherein R' is —S(O)$_2R^5$.

15. The compound of claim 1, wherein R' is —NO$_2$.

16. The compound of claim 13 or 14, wherein $R^5$ is optionally substituted $C_{1-6}$ aliphatic.

17. The compound of claim 16, wherein $R^5$ is methyl.

18. The compound of claim 16, wherein $R^5$ is —CF$_3$.

19. The compound of claim 13 or 14, wherein $R^5$ is optionally substituted phenyl.

20. The compound of claim 1, wherein X is O.

21. The compound of claim 1, wherein X is S.

22. The compound of claim 1, wherein the compound is of formula I-a or I-b:

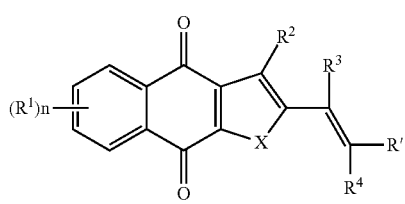

I-a

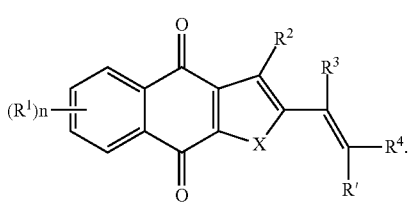

I-b

23. The compound of claim 1, wherein the compound is of formula I-c, I-d, I-e, or I-f:

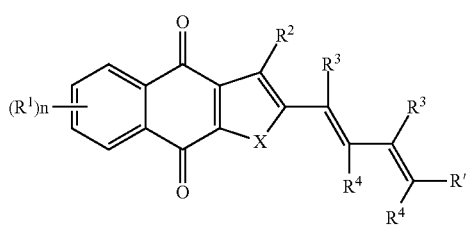

I-c

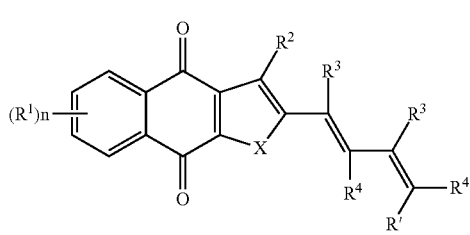

I-d

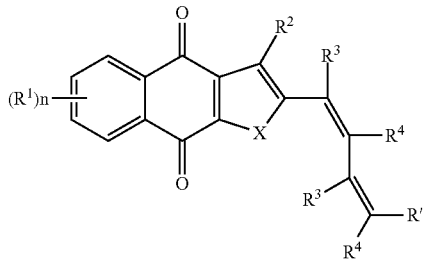

I-e

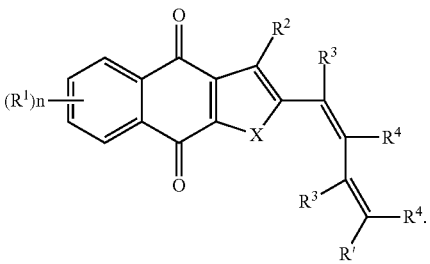

I-f

24. The compound of claim 1, selected from the group consisting of:

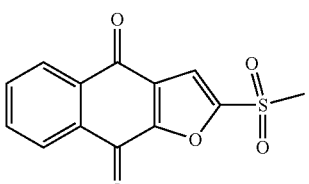

compound I

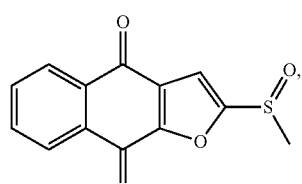

compound II

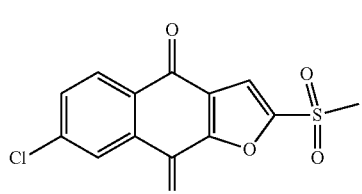

compound III

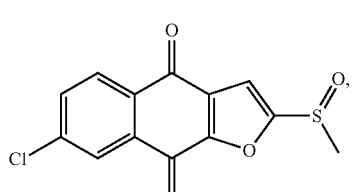

compound IV

-continued
compound V
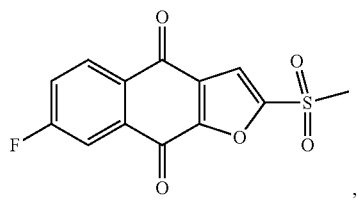,
compound VI
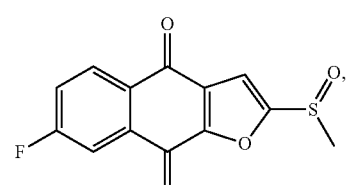,
compound VII
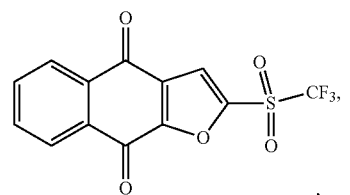,
compound VIII
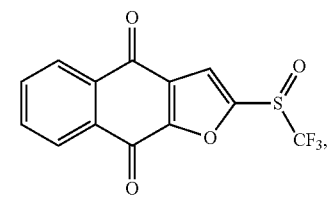,
compound IX
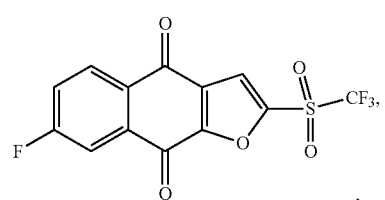,
compound X
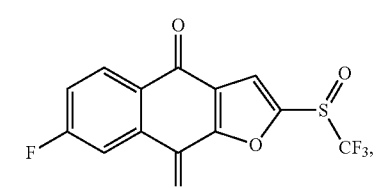,
compound XI
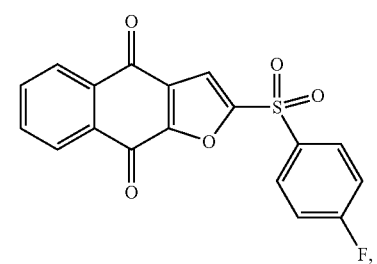,
-continued
compound XII
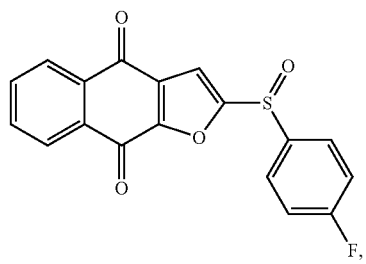,
compound XIII
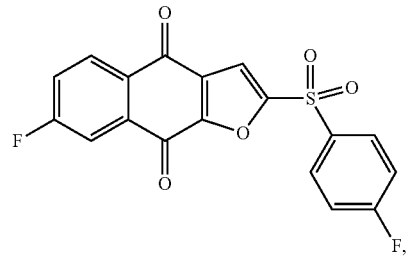,
compound XIV
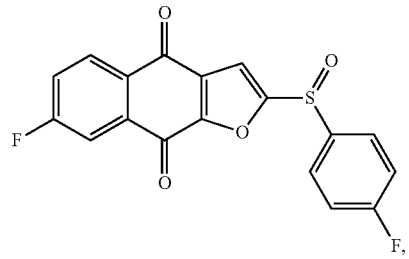,
compound XV
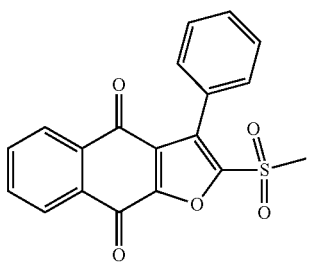,
compound XVI
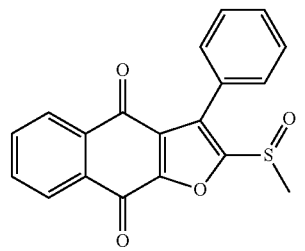,
compound XVII
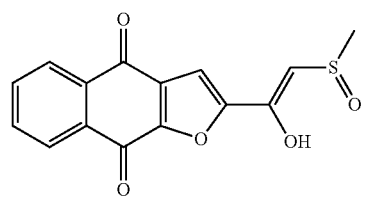 [SMILES: CS(=O)/C=C(\O)c1cc2c(o1)C(=O)c1ccccc1C2=O]

-continued
compound XVIII
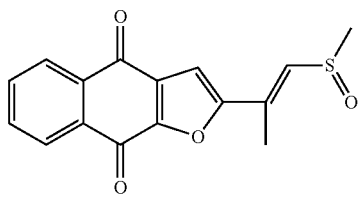 [SMILES: C/C(=C\S(C)=O)c1cc2c(o1)C(=O)c1ccccc1C2=O]
compound XIX
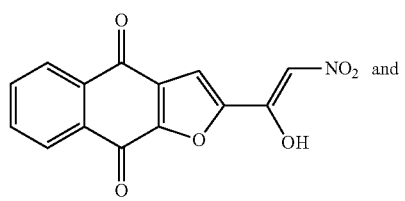
and
compound XX
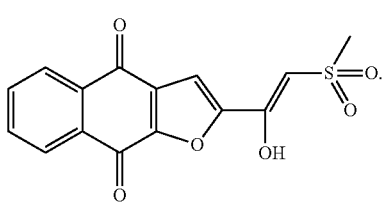 [SMILES: CS(=O)(=O)/C=C(\O)c1cc2c(o1)C(=O)c1ccccc1C2=O]
25. A pharmaceutical composition comprising a compound of claim 1, or a pharmaceutically acceptable salt thereof, and a pharmaceutically acceptable excipient, carrier, or diluent.
* * * * *